(12) United States Patent
Klein et al.

(10) Patent No.: US 6,225,091 B1
(45) Date of Patent: *May 1, 2001

(54) MULTIMERIC HYBRID GENE ENCODING A CHIMERIC PROTEIN WHICH CONFERS PROTECTION AGAINST PARAINFLUENZA VIRUS AND RESPIRATORY SYNCTIAL VIRUS

(75) Inventors: Michel H. Klein, Willowdale; Run-Pan Du, Thornhill; Mary E. Ewasyshyn, Willowdale, all of (CA)

(73) Assignee: Connaught Laboratories Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 08/001,554

(22) Filed: Jan. 6, 1993

(30) Foreign Application Priority Data

Jan. 6, 1992 (GB) .................................................. 9200117

(51) Int. Cl.$^7$ .............................. C12P 21/06; C12N 1/20; C12N 15/00; C07H 21/04
(52) U.S. Cl. ............... 435/69.3; 435/252.3; 435/252.32; 435/253.1; 435/320.1; 435/325; 536/23.4; 536/23.7
(58) Field of Search ............................... 435/69.3, 320.1, 435/252.3, 252.32, 253.1, 325; 935/32, 27, 12; 536/23.7, 23.4

(56) References Cited

U.S. PATENT DOCUMENTS

| 4,722,848 | * | 2/1988 | Paoletti et al. |
| 4,879,213 | * | 11/1989 | Fox et al. |
| 5,110,587 | * | 5/1992 | Paoletti et al. |

FOREIGN PATENT DOCUMENTS

| 0421626 | 4/1991 | (EP) . |
| WO89/05823 | 6/1989 | (WO) . |
| WO89/10405 | 11/1989 | (WO) . |
| 90/03437 | 4/1990 | (WO) . |
| WO93/21310 | 10/1993 | (WO) . |

OTHER PUBLICATIONS

Chanock et al Pediatrics 90(1):137, Jul. 1992.
Kasel et al Journal of Virology vol. 52(3) pp. 828–832, Dec. 1984.
Murphy et al; Experimental Lung Research. 2:97–109 (1981).
Porter et al; J. of Virology, Jan. 1991, p. 103–111, vol. 65, No. 1 (Jan. 1991).
Prince et al; Am.J. of Pathology, vol. 93, #3, 771–783 (Dec., 1978).
Prince et al; J. of Virology 57:721–728 (Mar. 1986).
Kapikian et al Am. J. Epidemiology 89, 1969, p. 405–421.
Belshe et al J. Inf. Dis. 145, 1982, p. 311–319.
Ray et al., (1989), Virus Research, 12: 169–180.
Coelingh et al., (1987), Virology, 160: 465–472.
Wathen et al., (1989), J. of Inf. Dis. 159: 255–263.
Spriggs et al., (1987), J. Virol. 61: 3416–3423.
Stott et al., (1987), J. Virol. 61: 3855–3861.
Wathen et al., (1989), J. Gen. Virol. 70: 2625–2635.
Brideau et al., (1989), J. Gen. Virol. 70: 2637–2644.
Conners et al., (1992) Vaccine 10: 475–484.
Perkus et al. (1989), J. Virology 63: 3829–3836.
Goebel et al., (1990) Virology 179: 247–266.
Perkus et al. (1990) Virology 179: 276–286.
Goebel et al., (1990) Virology 179: 517–563.
Tartaglia et al. (1992), Virology 188: 217–232.
Piccini et al. (1987), Methods in Enzymology, 153: 545–563.
Taylor et al., (1990), J. Virology 64: 1441–1450.
J. Virol. vol. 64, No. 8, 1990, pp. 4007–4012 P. Collins 'O glycosylation of glycoprotein g of human respiratory syncytial virus is specified within the divergen ectodomain'.
Mol. Cell. Biol. vol. 8, No. 4, 1988, pp. 1709–1714 S. Vijaya et al. 'Transport to the cell surface of a peptide sequence attached to the truncated C terminus of an n–terminally anchored integral membrane protein'.
Coelingh et al. J. Virol. 64(8):3833–43 (see abstract), 1990.
Hendry et al. J. Gen. Virol. 66(8):1705–14, 1985.
Hall et al. Science 265:1393–1394 Sep. 1994.
Ray et al. J. Infect. Dis 157(47):648–54 1988.
Stover et al. Nature 351:456–460 Jun. 6, 1991.
Olmstead et al. PNAS 83:7462–7466 1986.
Bowie et al. Science 247:1306–1310 1990.
Kumar et al. PNAS 87:1337–1341 (1990).

* cited by examiner

Primary Examiner—Anthony C. Caputa
Assistant Examiner—Mark Navarro
(74) Attorney, Agent, or Firm—Sim & McBurney

(57) ABSTRACT

Multimeric hybrid genes encoding the corresponding chimeric protein comprise a gene sequence coding for an antigenic region of a protein from a first pathogen linked to a gene sequence coding for an antigenic region of a protein from a second pathogen. The pathogens particularly are parainfluenza virus (PIV) and respiratory syncytial virus (RSV). A single recombinant immunogen is capable of protecting infants and similar susceptible individuals against diseases caused by both PIV and RSV.

20 Claims, 39 Drawing Sheets

FIG.1A. NUCLEOTIDE SEQUENCE OF THE PIV-3 F GENE (PCR-AMPLIFIED)

```
AAGTCAATACCAACAACTATTAGCAGTCATACGTGCAAGAACAAGAAGAGATTCAA
TTCAGTTATGGTTGTTGATAATCGTCAGTATGCACGTTCTTCTTCTCTAAGTT
        10        20        30        40        50        60

AAGCTAAATAAGAGAAATCAAGTTTTTATTCTCTTTTGTTTTCCATATAGAACACCCGAACAACAAAATCAAAA
TTCGATTTATTCTCTTTTAGTTCAAAAATAAGGTATATCTTGTGGGCTTGTTGTTTTAGTTTT
        70        80        90        100       110       120

CATCCAATCCATTTTAAACAAAAATTTCAAAGGTTTCTCTGGCCGTTGTTCGTGGTTTG
GTAGGTTAGGTAAAATTTGTTTTTTAAAGTTTCCAAAGAGACCGGCAACACAAGCACCAAAC
        130       140       150       160       170       180
                   SP
            MET PRO THR [LEU] ILE LEU LEU ILE ILE THR THR MET ILE MET ALA [SER] SER CYS GLN
        ACAATGCCAACTTTAATACTGCTAATTATTACAACAATGATTATGGCATCTTCCTGCCAA
        TGTTACGGTTGAAATTATGACGATTAATAATGTTGTTACTAATACCGTAGAAGGACGGTT
        190       200       210       220       230       240

ILE ASP ILE THR LYS LEU LEU GLN HIS VAL GLY VAL LEU VAL ASN SER PRO LYS GLY MET LYS
ATACATATCACAAAACTACAGCATGGTGTATTGGTCAACAGTCCCAAAGGGATGAAG
TATGTATAGTGTTTTGATGTCGTACCATCCAGCTAGTTCAGGTTCCCTACTTC
        250       260       270       280       290       300

ILE SER GLN ASN PHE GLU THR ARG TYR LEU ILE LEU SER LEU ILE LEU PRO LEU ILE GLU ASP
ATATCACAAAACTTCGAAACAAGATATCTAATTTTGAGCCTCATACCAAAAATAGAAGAC
TATAGTGTTTTGAAGCTTTGTTCTATAGATTAAAAACTCGGAGTATGGTTTTATCTTCTG
        310       320       330       340       350       360

SER ASN SER CYS GLY ASP GLN GLN ILE LYS GLN TYR LYS ARG LEU LEU ASP ARG LEU ILE
TCTAACTCTTGTGGTGACCAACAAATCAAACAAGAGGTTATTGGATAGACTGATC
AGATTGAGAACACCACTGGTTCTAGTCTGTTGTTATGTTTTCCAATAACCTATCTGACTAG
        370       380       390       400       410       420
```

FIG. 1B.

```
      ILE PRO LEU TYR ASP GLY LEU ARG LEU GLN LYS ASP VAL ILE VAL THR  ASN GLN GLU SER
      ATCCCTCTATATGATGGATTAAGATTACAGAAAGATGTGATAGTAACCAATCAAGAATCC
               430              440             450             460             470             480
      TAGGGAGATATACTACCTAATTCTAATGTCTTTCTACACTATCATTGGTTAGTTCTTAGG
                                              F2-F1 CLEAVAGE SITE
      ASN GLU ASN THR ASP PRO ARG THR ARG ARG↓SER PHE GLY GLY VAL ILE GLY THR ILE ALA
      AATGAAAACACTGATCCCAGAACAAGACGATCCTTTGGAGGGTAATTGGAGGTAACCATTGCT
                     490             500             510             520             530             540
      TTACTTTTGTGACTAGGGTCTTGTTCTGCTAGGAAACCTCCCCATTAACCTTGGTAACGA

LEU GLY VAL ALA THR SER ALA GLN ILE THR ALA ALA VAL ALA LEU VAL ALA LYS GLU ALA LYS GLN
      CTGGGAGTAGCAACCTCAGCACACAATTACAGCGGCAGTTGCTCTTGGTTGAAGCCAAGCAG
                550             560             570             580             590             600
      GACCCTCATCGTTGGAGTCGTGTTAATGTCGCCGTCAACGAGACCAACTTCGGTTCGTC

ALA LYS SER ASP ILE GLU LYS LEU LYS GLU ALA LEU ARG ASP THR ASN LYS ALA VAL GLN
      GCAAAATCACACATCGAAAAACTCAAAGAAGCAATCAGGGACACAAACAAAGCAGTGCAG
                610             620             630             640             650             660
      CGTTTTAGTGTGTAGCTTTTGAGTTTCTTCGTTAGTCCCTGTGTTTGTTCGTCACGTC

SER VAL GLN SER SER ILE GLY ASN LEU ILE VAL ALA ILE LYS SER VAL GLN ASP TYR VAL
      TCAGTTCAGAGCTCTATAGGAAATTTAATAGTAGCAATTAAATCAGTCCAAGATTATGTC
                670             680             690             700             710             720
      AGTCAAGTCTCGAGATATCCTTTAAATTATCATCGTTAATTTAGTCAGGTTCTAATACAG

ASN ASN GLU ILE VAL PRO SER ILE ALA ARG LEU GLY CYS GLU ALA ALA GLY LEU GLN LEU
      AACAACGAAATCGTGCCATCGATTGCTAGACTAGGTTGTGAAGCAGGACTTCAATTA
                730             740             750             760             770             780
      TTGTTGCTTTAGCACGGTAGCTAACGATCGATCCAACACTTCGTCCTGAAGTTAAT

GLY ILE ALA LEU THR GLN HIS TYR SER GLU LEU THR ASN ILE PHE GLY ASP ASN ILE GLY
      GGAATTGCATTAACACAGCATTACTCAGAATTAACAAACATATTTGGTGATAACATAGGA
                790             800             810             820             830             840
      CCTTAACGTAATTGTGTCGTAATGAGTCTTAATTGTTTGTATAAACCACTATTGTATCCT
```

FIG. 1C.

```
SER LEU GLN GLU LYS GLY ILE LYS LEU GLN GLY ILE ALA SER LEU TYR ARG THR ASN ILE
TCGTTACAAGAAAAAGGAATAAAATTACAAGGTATAGCATCATTATACCGCACAAATATC
AGCAATGTTCTTTTTCCTTATTTAATGTTCCATATCGTAGTAATATGGCGTGTTTATAG
     850                860                870                880                890       900

THR GLU ILE PHE THR THR SER THR VAL ASP LYS TYR ASP ILE TYR ASP LEU LEU PHE THR
ACAGAAATATTCACACAACATCAACACAGTTGATAAATATGATATCTATGATCTATTTACA
TGTCTTTATAAGTGTTGTTGTAGTTGTCAACTATTTATACTATAGATACTAGATAAATGT
     910                920                930                940                950       960

GLU SER ILE LYS VAL ARG VAL ILE ASP VAL ASP LEU ASN ASP TYR SER ILE THR LEU GLN
GAATCAATAAAGGTGAGAGTTATAGATGTTGATTTGAATGATTACTCAATCACCCTCCAA
CTTAGTTATTTCCACTCTCAATATCTACAACTAAACTTACTAATGAGTTAGTGGGAGGTT
     970                980                990                1000                1010      1020

VAL ARG LEU PRO LEU LEU THR ARG LEU LEU ASN THR GLN ILE TYR [LYS] VAL ASP SER ILE
GTCAGACTCCCTTATTAACTAGGCTGCTGAACACTCAGATCTACAAAGTAGATTCCATA
CAGTCTGAGGGAATAATTGATCCGACGACTTGTGAGTCTAGATGTTCATCTAAGGTAT
     1030               1040               1050               1060                1070      1080

SER TYR ASN ILE GLN ASN ARG GLU TRP TYR ILE PRO LEU PRO SER HIS ILE MET THR LYS
TCATATAATATCCAAAACAGAGAATGGTATATCCCTCTTCCCAGCCATATCATGACGAAA
AGTATATTATAGGTTTTGTCTCTTACCATATAGGGAGAAGGGTCGGTATAGTACTGCTTT
     1090               1100               1110               1120                1130      1140

GLY ALA PKE LEU GLY GLY ALA ASP VAL LYS GLU CYS ILE GLU ALA PHE SER SER TYR ILE
GGGCATTTCTAGGTGGAGCAGATGTCAAGGAATGTATAGAAGCATTCAGCAGTTATATA
CCCCGTAAAGATCCACCTCGTCTACAGTTCCTTACATATCTTCGTAAGTCGTCAATATAT
     1150               1160               1170               1180                1190      1200

CYS PRO SER ASP PRO GLY PHE VAL LEU ASN HIS GLU KET GLU SER CYS LEU SER GLY ASN
TGCCCTTCTGATCCAGGATTTGTACTAAACCATGAAATGGAGAGCTGCTTATCAGGAAAC
ACGGGAAGACTAGGTCCTAAACATGATTTGGTACTTTACCTCTCGACGAATAGTCCTTTG
     1210               1220               1230               1240                1250      1260
```

FIG.1D.

```
ILE SER GLN CYS PRO ARG THR THR VAL SER ASP ILE VAL PRO ARG TYR ALA PHE VAL
ATATCCCAATGTCCAAGAACCACGGTCACATCAGACACATTGTTCCAAGATATGCATTCGTC
TATAGGGTTACAGGTTCTTGGTGCCAGTGTAGTCTGTAACAAGGTTCTATACGTAAGCAG
           1270         1280         1290         1300         1310         1320

ASN GLY GLY VAL VAL ALA ASN CYS ILE THR THR THR CYS THR CYS ASN GLY ILE ASP ASN
AATGGAGGAGTGGTTGCAAACTGTATAACAACCACCTGTACATGCAACGGAATCGACAAT
TTACCTCCTCACCAACGTTTGACATATTGTTGGTGGACATGTACGTTGCCTTAGCTGTTA
           1330         1340         1350         1360         1370         1380

ARG ILE ASN GLN PRO PRO ASP GLN GLY VAL LYS ILE ILE THR HIS LYS GLU CYS ASN THR
AGAATCAATCAACCACCTGATCAAGGAGTAAAAATTATAACACATAAAGAATGTAATACA
TCTTAGTTAGTTGGTGGACTAGTTCCTCATTTTTAATATTGTATTTCTTACATTATGT
           1390         1400         1410         1420         1430         1440

ILE GLY ILE ASN GLY MET LEU PHE ASN THR ASN LYS GLU GLY THR LEU ALA PHE TYR THR
ATAGGTATCAACGGAATGCTGTTCAATACAAATAAAGAAGGAACTCTTGCATTCTACACA
TATCCATAGTTGCCTTACGACAAGTTATGTTTATTTCTTCCTTGAGAACGTAAGATGTGT
           1450         1460         1470         1480         1490         1500

PRO ASN ASP ILE THR LEU ASN ASN SER VAL ALA LEU ASP PRO ILE SER ILE GLU
CCAAATGATATAACACTAAATAATTCTGTTGCACTTGATCCAATTGACATATCAATCGAG
GGTTTACTATATTGTGATTTATTAAGACAACGTGAACTAGGTTAACTGTATAGTTAGCTC
           1510         1520         1530         1540         1550         1560

LEU ASN LYS ALA LYS SER ASP LEU GLU SER LYS GLU TRP ILE ARG ARG SER ASN GLN
CTTAACAAGCCAAATCAGATCTAGAAGAATCAAAAGAATGGATAAGAAGGTCAAATCAA
GAATTGTTCGGTTTAGTCTAGATCTTCTTAGTTTTCTTACCTATTCTTCCAGTTTAGTT
           1570         1580         1590         1600         1610         1620

LYS LEU ASP SER ILE GLY ASN TRP HIS GLN SER SER THR THR ILE ILE ILE LEU ILE
AAACTAGATTCTATTGGAAACTGGCATCAATCTAGCACTACAATCATAATTATTTAATA
TTTGATCTAAGATAACCTTTGACCGTAGTTAGATCGTGATGTTAGTATTAATAAAATTAT
           1630         1640         1650         1660         1670         1680
                                                        TM
```

FIG.1E

```
MET ILE ILE ILE LEU PHE ILE ILE ASN VAL THR ILE ILE THR ILE ALA ILE LYS TYR TYR
ATGATCATTATATTGTTTATAATTAATGTAACGATAATTACAATTGCAATTAAGTATTAC
TACTAGTAATATAACAAATATTAATTACATTGCTATTAATGTTAACGTTAATTCATAATG
       1690      1700      1710      1720      1730      1740

ARG ILE GLN LYS ARG ASN ARG VAL ASP GLN ASN ASP LYS PRO TYR VAL LEU THR ASN LYS
AGAATTCAAAAGAGAAATCGAGTGGATCAAAATGACAAGCCATATGTACTAACAAACAAA
TCTTAAGTTTTCTCTTTAGCTCACCTAGTTTTACTGTTCGGTATACATGATTGTTTGTTT
       1750      1760      1770      1780      1790      1800

TGACATATCTATAGATCATTAGATATTAAAATTATAAAAACTT
ACTGTATAGATATCTAGTAATCTATAATTTTAATATTTTTGAA
       1810      1820      1830      1840
```

NUCLEOTIDE SEQUENCE OF THE PIV-3 F GENE. THE cDNA SEQUENCE IS SHOWN IN THE PLUS (mRNA) STRAND SENSE IN THE 5' TO 3' DIRECTION. THE SIGNAL PEPTIDE (SP) AND THE TRANSMEMBRANE (TM) ANCHOR DOMAIN ARE UNDERLINED. THE PREDICTED F2-F1 CLEAVAGE SITE IS INDICATED BY THE ARROW (↓). AMINO ACIDS DIFFERING FROM THE PUBLISHED PRIMARY SEQUENCE OF THE PROTEIN ENCODED BY THE PIV-3 F GENE ARE BOXED.

FIG. 3A. NUCLEOTIDE SEQUENCE OF THE PIV-3 HN GENE.

```
                         MET GLU TYR TRP LYS HIS THR ASN HIS GLY LYS ASP ALA GLY
5' AGACAAATCCAAATTCGAGATGGAATACTGGAAGCATACCAATCACGGAAAGGATGCTGG
   TCTGTTTAGGTTTAAGCTCTACCTTATGACCTTCGTATGGTTAGTGCCTTTCCTACGACC
           10        20        30        40        50        60
                                                        —TM—→

ASN GLU LEU GLU THR GLY ARG THR SER MET ALA THR ASN GLY ASN LYS LEU THR ASN LYS ILE THR TYR
CAATGAGCTGGAGACGGGACGTCCATGGCTACTAATGGCAACAAGCTCACCAATAAGATAACATA
GTTACTCGACCTCTGCCAGGTACCGATGATTACCGTTGTTCGAGTGGTTATTCTATTGTAT
        70        80        90       100       110       120

ILE LEU TRP THR ILE ILE LEU VAL LEU LEU SER ILE VAL PHE ILE ILE VAL LEU ILE ASN
TATTATTGGACAATAATCCTGGTGTTATTATCAATAGTCTTCATCATAGTACGATTAATTAA
ATATAATACCTGTTATTAGGACCACAATAATAGTTATCAGAAGTATCACGATTAATT
       130       140       150       160       170       180

SER ILE LYS SER GLU LYS ALA HIS GLU SER LEU LEU LEU ALA SER ASP ILE ASN ASN GLU PHE MET
TTCCATCAAATTTTCACTTTTCGAAAAGTGAAAAGGCTCATGAATCATTGCTGCAAGACATAAATAATGAGTTTAT
AAGGTAGTTTAAAAGTGAAAAGCTTTTCACTTTTCCGAGTACTTAGTAACGACGTTCTGTATTATTACTCAAATA
       190       200       210       220       230       240

GLU ILE THR GLU LYS ILE GLN MET ALA SER ASP ASN ILE ASN ASP LEU ILE GLN SER GLY
GGAAATTACAGAGAAAAGATCCAAATGGCATCGGATAATATCGGATCTAATACAGTCAGG
CCTTTAATGTCTCTTTTCTAGGTTTACCGTAGCCTATTATAGCCTAGATTATGTCAGTCC
       250       260       270       280       290       300

VAL ASN THR ARG LEU LEU THR ILE GLN SER HIS VAL GLN ASN TYR ILE PRO ILE SER LEU
AGTGAATACAAGGCTTCTTACAATTCAGAGTCATGTCCAGAATTATATACCAATATCACT
TCACTTATGTTCCGAAGAATGTTAAGTCTCAGTACAGGTCTTAATATATGGTTATAGTGA
       310       320       330       340       350       360
```

```
CYS  ILE  THR  HIS  TYR  ASN  LYS  GLY  TYR  CYS  PHE  HIS  ILE  VAL  GLU  ILE  ASN  [GLN] LYS  SER
CTGCATCACACTATAACAAAGGATATTGTTTTCATATAGTAGAAATAAATCAGAAAAG
GACGTAGTGTGTGATATTGTTCCTATAACAAAAGTATATCATCTTTATTTAGTCTTTC
       1630              1640              1650              1660              1670              1680

LEU [ASN] THR [LEU] GLN  PRO  MET  LEU  PHE  LYS  THR  GLU  [VAL] PRO  LYS  SER  CYS  SER  ***
CTTAACACACTTCAACCCATGTTGTTCAAGACAGAGGTTCCAAAAAGCTGCAGTTAATC
GAATTTGTGTGAAGTTGGGTACAACAAGTTCTGTCTCCAAGGTTTTTCGACGTCAATTAG
       1690              1700              1710              1720              1730              1740

ATAATTAACCGCAATATGCATTAACCTATCTATAATAACAAGTATATGATAAGTAATCAGC
TATTAATTGGCGTTATACGTAATTGGATAGATATTATGTTCATATATTCATTAGTCG
       1750              1760              1770              1780              1790              1800

AATCAGACAATAGACAAAAGGGAAATATAAAAA
TTAGTCTGTTATCTGTTTTCCCTTTATATTTT
       1810              1820              1830
```

NUCLEOTIDE SEQUENCE OF THE PIV-3 HN GENE. THE cDNA SEQUENCE
IS SHOWN IN THE PLUS (mRNA) STRAND SENSE IN THE 5' TO 3'
DIRECTION. THE TRANSMEMBRANE (TM) ANCHOR DOMAIN IS UNDERLINED. AMINO ACIDS
DIFFERING FROM THE PUBLISHED PRIMARY SEQUENCE OF THE PROTEIN ENCODED BY THE PIV-3
HN GENE ARE BOXED.

FIG.3E.

RESTRICTION MAP OF THE PIV-3 HN GENE

FIG.5A.  NUCLEOTIDE SEQUENCE OF THE RSV F GENE.

```
         SP
5' MET GLU LEU  PRO  ILE LEU LYS ALA ASN ALA ILE THR THR ILE LEU ALA  ALA  VAL THR PHE
   ATG GAG TTG CCA ATC CTC AAA GCA AAT GCA ATT ACC ACA ATC CTC GCT GCA GTC ACA TTT
                       10                   20                   30                   40                   50                   60
   TAC CTC AAC GGT TAG GAG TTT CGT TTA CGT TAA TGG TGT TAG GAG CGA CGT CAG TGT AAA

CYS PHE ALA  SER  SER GLN ASN ILE THR GLU GLU PHE TYR GLN SER THR CYS SER ALA VAL
TGC TTT GCT TCT AGT CAA AAA CAT CAC TGA AGA ATT TTA TCA ATC AAC ATG CAG TGC AGT T
                       70                   80                   90                  100                  110                  120
ACG AAA CGA AGA TCA GTT GTT TTT GTA GTG ACT TCT TAA AAT AGT TAG TTG TAC GTC ACG TCA A

SER LYS GLY TYR LEU SER ALA LEU ARG THR GLY TRP TYR THR TYR THR SER VAL ILE THR ILE GLU
AGC AAA GGC TAT CTT AGT GCT CTA AGA ACT GGT TGG TAT ACT AGT GTT ATA ACT ATA GAA
                      130                  140                  150                  160                  170                  180
TCG TTT CCG ATA GAA TCA CGA GAT TCT TGA CCA ACC ATA TGA TCA CAA TAT TGA TAT CTT

LEU SER ASN ILE LYS GLU ASN LYS CYS ASN GLY THR ASP ALA LYS VAL LYS LEU  MET  LYS
TTA AGT AAT ATA TCA AGG AAA ATA AGT GTA ATG GAA CAG ATG CTA AGG TAA AAT TGA TGA AA
                      190                  200                  210                  220                  230                  240
AAT TCA TTA TAG TTC CTT TAT TCA CAT TAC CTT GTC TAC GAT TCC ATT TTA ACT ACT TT

GLN GLU LEU ASP LYS TYR LYS ASN ALA VAL THR GLU LEU GLN LEU LEU MET GLN SER THR
CAA GAA TTA GAT AAA TAT AAA AAT GCT GTA ACA GAA TTG CAG TTG CTC ATG CAA AGC ACA
                      250                  260                  270                  280                  290                  300
GTT CTT AAT CTA TTT ATA TTT TTA CGA CAT TGT CTT AAC GTC TTA ACG AGT ACG TTT CGT GT

PRO  ALA   ALA  ASN ASN ARG ALA ARG ARG GLU LEU PRO ARG PHE MET ASN TYR THR LEU ASN
CCA GCA GCA AAC AAT CGA GCT AGC CAG AAG AAC TAC CAA GGT TTA TGA ATT ATA CAC TCA AC
                      310                  320                  330                  340                  350                  360
GGT CGT CGT TTG TTA GCT CGA TCG GTC TTC TTG ATG GTT CCA AAT ACT TAA TAT GTG AGT TG
```

```
                                                               F2-F1 CLEAVAGE SITE
ASN [THR] LYS LYS THR ASN VAL THR LEU SER LYS LYS ARG ARG↓PHE LEU GLY PHE
AAT ACC AAA AAA ACC AAT GTA ACA TTA AGC AAG AAA AGA AGA AGA TTT CTT GGT TTT
TTA TGG TTT TTT TGG TTA CAT TGT AAT TCG TTC TTT CTT CTA AAG AAC CAA AA
              370              380              390              400              410              420

LEU LEU GLY VAL GLY SER ALA [ILE] ALA VAL SER LYS VAL LEU HIS LEU
TTG TTA GGT GTT GGA TCT GCA ATC GCT GTG TAT CTA AGG TCC TGC ACT TA
AAC AAT CCA CAA CCT AGA CGT TAG CGA CAC ATA GAT TCC AGG ACG TGA AT
              430              440              450              460              470              480

GLU GLY VAL ASN LYS ILE LYS SER ALA LEU LEU SER THR ASN LYS ALA VAL VAL SER
GAA GGA GAA GTG AAC AAG ATC AAA AGT GCT CTA CTA TCC ACA AAC AAG CCG TAG TCA GC
CTT CCT CTT CAC TTG TTC TAG TTT TCA CGA GAT GAT AGG TGT TTG TTC GGC ATC AGT CG
              490              500              510              520              530              540

LEU SER ASN GLY VAL SER VAL LEU THR SER LYS VAL LEU ASP LEU LYS ASN TYR ILE ASP
TTA TCA AAT GGA GTT AGT GTC TTA ACC AGC AAA GTG TTA GAC CTC AAA AAC TAT ATA GAT
AAT AGT TTA CCT CAA TCA CAG AAT TGG TCG TTT CAC AAT CTG GAG TTT TGA TAT ATC TA
              550              560              570              580              590              600

LYS GLN LEU LEU PRO ILE VAL ASN LYS GLN SER CYS [ARG] ILE SER ASN ILE GLU THR VAL
AAA CAA TTG TTA CCT ATT GTG AAT AAG CAA AGC TGC AGA ATA TCA AAT ATA GAA ACT GTG
TTT GTT AAC AAT GGA TAA CAC TTA TTC GTT TCG ACG TCT TAT AGT TTA TAT CTT TGA CAC
              610              620              630              640              650              660

ILE GLU PHE GLN HIS LYS ASN ASN ARG LEU LEU GLU ILE THR ARG GLU PHE SER VAL ASN
ATA GAG TTC CAA CAA AAG AAC AAC AGA CTA CTA GAG ATT ACC AGG GAA TTT AGT GTT AAT
TAT CTC AAG GTT GTT TTC TTG TTG TCT GAT GAT CTC TAA TGG TCC CTT AAA TCA CAA TTA
              670              680              690              700              710              720

ALA GLY VAL THR THR PRO VAL SER THR TYR MET LEU THR ASN SER GLU LEU LEU SER LEU
GCA GGT GTA ACT ACA CCT GTA AGC ACT TAC ATG TTA ACT AAT AGT GAA TTA TTG TCA TTA
CGT CCA CAT TGA TGT GGA CAT TCG TGA ATG TAC AAT TGA TTA TCA CTT AAT AAC AGT AAT
              730              740              750              760              770              780
```

```
ILE ASN ASP MET PRO ILE THR ASN ASP GLN LYS LYS LEU MET SER ASN ASN VAL GLN ILE
ATCAATGATATGCCTATAACAAATGATCAGAAAAAAGTTAATGTCCAACAATGTTACAAGTTAT
             790                800               810               820               830            840
TAGTTACTATACGGATATATTGTTTACTAGTCTTTTTCAATTACAGGTTGTTACAAGTTTAT

VAL ARG GLN GLN SER TYR SER ILE MET SER ILE ILE LYS GLU VAL LEU ALA TYR VAL
GTTAGACAGCAAAGTTACTCTATCATGTCCATAATAAAAGAGGAAGTCTTAGCATATGTA
             850               860               870               880               890            900
CAATCTGTCGTTTCAATGAGATAGTACAGGTATTATTTTCTCCTTCAGAATCGTATACAT

VAL GLN LEU PRO LEU TYR GLY VAL ILE ASP THR PRO CYS TRP LYS LEU HIS THR SER PRO
GTACAATTACCACTATATGGTGTGATAGATACACCCTTGTTGGAAATTACACACATCCCT
             910               920               930               940               950            960
CATGTTAATGGTGATATACCACACTATCTATGTGGAACAACCTTTAATGTGTGTAGGGGA

LEU CYS THR THR ASN THR LYS GLU GLY SER ASN ILE CYS LEU THR ARG THR ASP ARG GLY
CTATGTACAACCAACACAAAAGAAGGGTCAAACATCTGTTTAACAAGAACTGACAGAGGA
             970               980               990              1000              1010           1020
GATACATGTTGGTTGTGTTTTCTTCCCAGTTTGTAGACAAATTGTTCTTGACTGTCTCCT

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAGTT
            1030              1040              1050              1060              1070           1080
ACCATGACACTGTTACGTCCTAGTCATAGAAAGAAGGGTGTTCGACTTTGTACATTTCAA

GLN SER ASN ARG VAL PHE CYS ASP THR MET ASN SER LEU THR LEU PRO SER GLU [VAL] ASN
CAATCGAGTCGAGTATTTTGTGACAATGAACAGTTTAACATTACCAAGTGAAGTAAAT
            1090              1100              1110              1120              1130           1140
GTTAGCTTCAGCTCATAAAACACTGTTACTTGTCAAATTGTAATGGTTCACTTCATTTA

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAAACA
            1150              1160              1170              1180              1190           1200
GAGACGTTACAACTGTATAAGTTAGGGTTTATACTAACATTTTAATACTGAAGTTTTTGT
```

```
ASP VAL SER SER SER VAL ILE THR SER LEU GLY ALA ILE VAL SER CYS TYR GLY LYS THR
GATGTAAGCAGCTCCGTTATCACATCTCTAGGAGCCATTGTGTCATGCTATGGCAAAACT
        1210              1220              1230              1240              1250              1260

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTCTAACGGGTGTGAT
        1270              1280              1290              1300              1310              1320

TYR VAL SER ASN LYS GLY [VAL] ASP THR VAL SER VAL GLY ASN THR LEU TYR TYR VAL ASN
TATGTATCAAATAAAGGGGTGGACACTGTGTCTGTAGGTAACACATTATATTATGTAAAT
        1330              1340              1350              1360              1370              1380

LYS GLN GLY LYS SER LEU TYR VAL LYS GLY GLU PRO ILE ILE ASN PHE TYR ASP PRO
AAGCAAGAAGGCAAAAGTCTCTATGTAAAGGGTGAACCAATAATTTCTATGACCCA
        1390              1400              1410              1420              1430              1440

LEU VAL PHE PRO SER ASP GLU PHE ASP ALA SER ILE SER GLN VAL ASN VAL ASN GLU LYS ILE ASN
TTAGTATTTCCCTCTGATGAATTTGATGCATCAATATCTCAAGTCAACGAGAAGATTAAC
        1450              1460              1470              1480              1490              1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
        1510              1520              1530              1540              1550              1560

SER THR THR ASN ILE MET ILE THR THR ILE ILE GLU ILE ILE VAL ILE LEU LEU SER
        TM
AGTCTCAAATCGTAAATAAGCATTTAGGCTACTTAATATCTCTAATACTATTAACAATAGT
        1570              1580              1590              1600              1610              1620
```

FIG.5D.

```
LEU  ILE  ALA  VAL  GLY  LEU  LEU  LEU  TYR  CYS  LYS  ALA  ARG  SER  THR  PRO  VAL  THR  LEU  SER
T T A A T T G C T G T T G G A C T G C T C C T A T A C T G T A A G G C C A G A A G C A C A C C A G T C A C A C T A A G C
A A T T A A C G A C A A C C T G A C G A G G A T A T G A C A T T C C G G T C T T C G T G T G G T C A G T G T G A T T C G
        1630                1640                1650                1660                1670                1680

LYS, ASP  GLN  LEU  SER  GLY  ILE  ASN  ASN  ILE  ALA  PHE  SER  ASN
A A G G A T C A A C T G A G T G G T A T A A A T A A T A T T G C A T T T A G T A A C T G A A T A A A A A T A G C A C C T
T T C C T A G T T G A C T C A C C A T A T T T A T T A T A A C G T A A A T C A T T G A C T T A T T T T T A T C G T G G A
        1690                1700                1710                1720                1730                1740

A A T C A T G T T C T T A C A A T G G T T T A C T A T C T G C T C A T A G A C A A C C C A T C T A T C A T T G G A T T T
T T A G T A C A A G A A T G T T A C C A A A T G A T A G A C G A G T A T C T G T T G G G T A G A T A G T A A C C T A A A
        1750                1760                1770                1780                1790                1800

T C T T A A A A T C T G A A C T T C A T C G A A A C T C T T A T C T A T A A A C C A T C T C A C T T A C A C T A T T T A
A G A A T T T T A G A C T T G A A G T A G C T T T G A G A A T A G A T A T T T G G T A G A G T G A A T G T G A T A A A T
        1810                1820                1830                1840                1850                1860

A G T A G A T T C C T A G T T T A T A G T T A T A T   3'
T C A T C T A A G G A T C A A A T A T C A A T A T A
        1870                1880
```

NUCLEOTIDE SEQUENCE OF THE RSV F GENE.THE cDNA SEQUENCE IS SHOWN IN THE PLUS (mRNA) STRAND SENSE IN THE 5' TO 3' DIRECTION.THE SIGNAL PEPTIDE (SP) AND THE TRANSMEMBRANE (TM) ANCHOR DOMAIN ARE UNDERLINED.THE PREDICTED F2-F1 CLEAVAGE SITE IS INDICATED BY THE ARROW (↓).AMINO ACIDS DIFFERING FROM THE PUBLISHED PRIMARY SEQUENCE OF THE PROTEIN ENCODED BY THE RSV F GENE ARE BOXED.

RESTRICTION MAP OF THE RSV F GENE

FIG.7A. NUCLEOTIDE SEQUENCE OF THE RSV G GENE

```
          MET SER LYS ASN LYS ASP GLN ARG
T G C A A A C A T G T C C A A A A A C A A G G A C C A A C G
A C G T T T G T A C A G G T T T T T G T T C C T G G T T G C
              10           20              30

THR ALA LYS THR LEU GLU [LYS] THR TRP ASP
C A C C G C T A A G A C A C T A G A A A A G A C C T G G G A
G T G G C G A T T C T G T G A T C T T T T C T G G A C C C T
            40              50              60

THR LEU ASN HIS LEU LEU PHE ILE SER SER
C A C T C T C A A T C A T T T A T T A T T C A T A T C A T C
G T G A G A G T T A G T A A A T A A T A A G T A T A G T A G
            70              80              90
                                               ←
   [GLY] LEU TYR LYS LEU ASN LEU LYS SER VAL
G G G C T T A T A T A A G T T A A A T C T T A A A T C T G T
C C C G A A T A T A T T C A A T T T A G A A T T T A G A C A
            100             110             120
─────────────── TM ───────────────
    ALA GLN ILE THR LEU SER ILE LEU ALA MET
A G C A C A A A T C A C A T T A T C C A T T C T G G C A A T
T C G T G T T T A G T G T A A T A G G T A A G A C C G T T A
            130             140             150
────────────────────────────────────
    ILE ILE SER THR SER LEU ILE ILE [THR] ALA
G A T A A T C T C A A C T T C A C T T A T A A T T A C A G C
C T A T T A G A G T T G A A G T G A A T A T T A A T G T C G
            160             170             180
                                       →
    ILE ILE PHE ILE ALA SER ALA ASN HIS LYS
C A T C A T A T T C A T A G C C T C G G C A A A C C A C A A
G T A G T A T A A G T A T C G G A G C C G T T T G G T G T T
            190             200             210

VAL THR [LEU] THR THR ALA ILE ILE GLN ASP
A G T C A C A C T A A C A A C T G C A A T C A T A C A A G A
T C A G T G T G A T T G T T G A C G T T A G T A T G T T C T
            220             230             240

ALA THR SER GLN ILE LYS ASN THR THR PRO
T G C A A C A A G C C A G A T C A A G A A C A C A A C C C C
A C G T T G T T C G G T C T A G T T C T T G T G T T G G G G
            250             260             270

THR TYR LEU THR GLN [ASP] PRO GLN LEU GLY
A A C A T A C C T C A C T C A G G A T C C T C A G C T T G G
T T G T A T G G A G T G A G T C C T A G G A G T C G A A C C
            280             290             300
```

FIG.7B.

```
      ILE  SER  [PHE] SER  ASN  [LEU] SER  GLU  ILE  THR
     A A T C A G C T T C T C C A A T C T G T C T G A A A T T A C
     T T A G T C G A A G A G G T T A G A C A G A C T T T A A T G
              310               320               330

SER  GLN  [THR] THR  THR  ILE  LEU  ALA  SER  THR
     A T C A C A A A C C A C C A C C A T A C T A G C T T C A A C
     T A G T G T T T G G T G G T G G T A T G A T C G A A G T T G
              340               350               360

THR  PRO  GLY  VAL  LYS  SER  [ASN] LEU  GLN  [PRO]
     A A C A C C A G G A G T C A A G T C A A A C C T G C A A C C
     T T G T G G T C C T C A G T T C A G T T T G G A C G T T G G
              370               380               390

THR  THR  VAL  LYS  THR  LYS  ASN  THR  THR  THR
     C A C A A C A G T C A A G A C T A A A A A C A C A A C A A C
     G T G T T G T C A G T T C T G A T T T T T G T G T T G T T G
              400               410               420

THR  GLN  THR  GLN  PRO  SER  LYS  PRO  THR  THR
     A A C C C A A A C A C A A C C C A G C A A G C C C A C T A C
     T T G G G T T T G T G T T G G G T C G T T C G G G T G A T G
              430               440               450

LYS  GLN  ARG  GLN  ASN  LYS  PRO  PRO  [ASN] LYS
     A A A A C A A C G C C A A A A C A A A C C A C C A A A C A A
     T T T T G T T G C G G T T T T G T T T G G T G G T T T G T T
              460               470               480

PRO  ASN  ASN  ASP  PHE  HIS  PHE  GLU  VAL  PHE
     A C C C A A T A A T G A T T T T C A C T T C G A A G T G T T
     T G G G T T A T T A C T A A A A G T G A A G C T T C A C A A
              490               500               510

ASN  PHE  VAL  PRO  CYS  SER  ILE  CYS  SER  ASN
     T A A C T T T G T A C C C T G C A G C A T A T G C A G C A A
     A T T G A A A C A T G G G A C G T C G T A T A C G T C G T T
              520               530               540

ASN  PRO  THR  CYS  TRP  ALA  ILE  CYS  LYS  ARG
     C A A T C C A A C C T G C T G G G C T A T C T G C A A A A G
     G T T A G G T T G G A C G A C C C G A T A G A C G T T T T C
              550               560               570

ILE  PRO  ASN  LYS  LYS  PRO  GLY  LYS  LYS  THR
     A A T A C C A A A C A A A A A A C C A G G A A A G A A A A C
     T T A T G G T T T G T T T T T T G G T C C T T T C T T T T G
              580               590               600
```

FIG. 7C.

```
       THR   THR   LYS   PRO   THR   LYS   LYS   PRO   THR   PHE
     C A C C A C C A A G C C T A C A A A A A A A C C A A C C T T
     G T G G T G G T T C G G A T G T T T T T T T G G T T G G A A
             610                 620                 630

LYS   THR   THR   LYS   LYS   ASP   [LEU]  LYS   PRO   GLN
     C A A G A C A A C C A A A A A A G A T C T C A A A C C T C A
     G T T C T G T T G G T T T T T T C T A G A G T T T G G A G T
             640                 650                 660

THR   THR   LYS   [PRO]  LYS   GLU   VAL   PRO   THR   THR
     A A C C A C T A A A C C A A A G G A A G T A C C C A C C A C
     T T G G T G A T T T G G T T T C C T T C A T G G G T G G T G
             670                 680                 690

LYS   PRO   THR   GLU   GLU   PRO   THR   ILE   ASN   THR
     C A A G C C C A C A G A A G A G C C A A C C A T C A A C A C
     G T T C G G G T G T C T T C T C G G T T G G T A G T T G T G
             700                 710                 720

THR   LYS   THR   ASN   ILE   [THR]  THR   THR   LEU   LEU
     C A C C A A A A C A A A C A T C A C A A C T A C A C T G C T
     G T G G T T T T G T T T G T A G T G T T G A T G T G A C G A
             730                 740                 750

THR   [ASN]  ASN   THR   THR   GLY   ASN   PRO   [LYS]  LEU
     C A C C A A C A A C A C C A C A G G A A A T C C A A A A C T
     G T G G T T G T T G T G G T G T C C T T T A G G T T T T G A
             760                 770                 780

THR   SER   GLN   MET   GLU   THR   PHE   HIS   SER   THR
     C A C A A G T C A A A T G G A A A C C T T C C A C T C A A C
     G T G T T C A G T T T A C C T T T G G A A G G T G A G T T G
             790                 800                 810

SER   SER   GLU   GLY   ASN   [LEU]  SER   PRO   SER   GLN
     C T C C T C C G A A G G C A A T C T A A G C C C T T C T C A
     G A G G A G G C T T C C G T T A G A T T C G G G A A G A G T
             820                 830                 840

VAL   SER   THR   THR   SER   GLU   [HIS]  PRO   SER   GLN
     A G T C T C C A C A A C A T C C G A G C A C C C A T C A C A
     T C A G A G G T G T T G T A G G C T C G T G G G T A G T G T
             850                 860                 870

PRO   SER   SER   PRO   PRO   ASN   THR   [THR]  ARG   GLN
     A C C C T C A T C T C C A C C C A A C A C A A C A C G C C A
     T G G G A G T A G A G G T G G G T T G T G T T G T G C G G T
             880                 890                 900
```

```
***
GTAGTTATTAAAAAAAAAA
CATCAATAATTTTTTTTTT
     910           920
```

NUCLEOTIDE SEQUENCE OF THE RSV G GENE. THE cDNA SEQUENCE IS SHOWN IN THE PLUS (mRNA) STRAND SENSE IN THE 5' TO 3' DIRECTION. THE TRANSMEMBRANE (TM) ANCHOR DOMAIN IS UNDERLINED. AMINO ACIDS DIFFERING FROM THE PUBLISHED PRIMARY SEQUENCE OF THE PROTEIN ENCODED BY THE RSV G GENE ARE BOXED.

FIG.7D.

RESTRICTION MAP OF RSV G GENE

5'—AflIII—AhaII———StanI—BamHI———PleI———NspV—PstI———BglII—EarI———AspHI———BsrI—3' bp  250  500  750

FIG. 8.

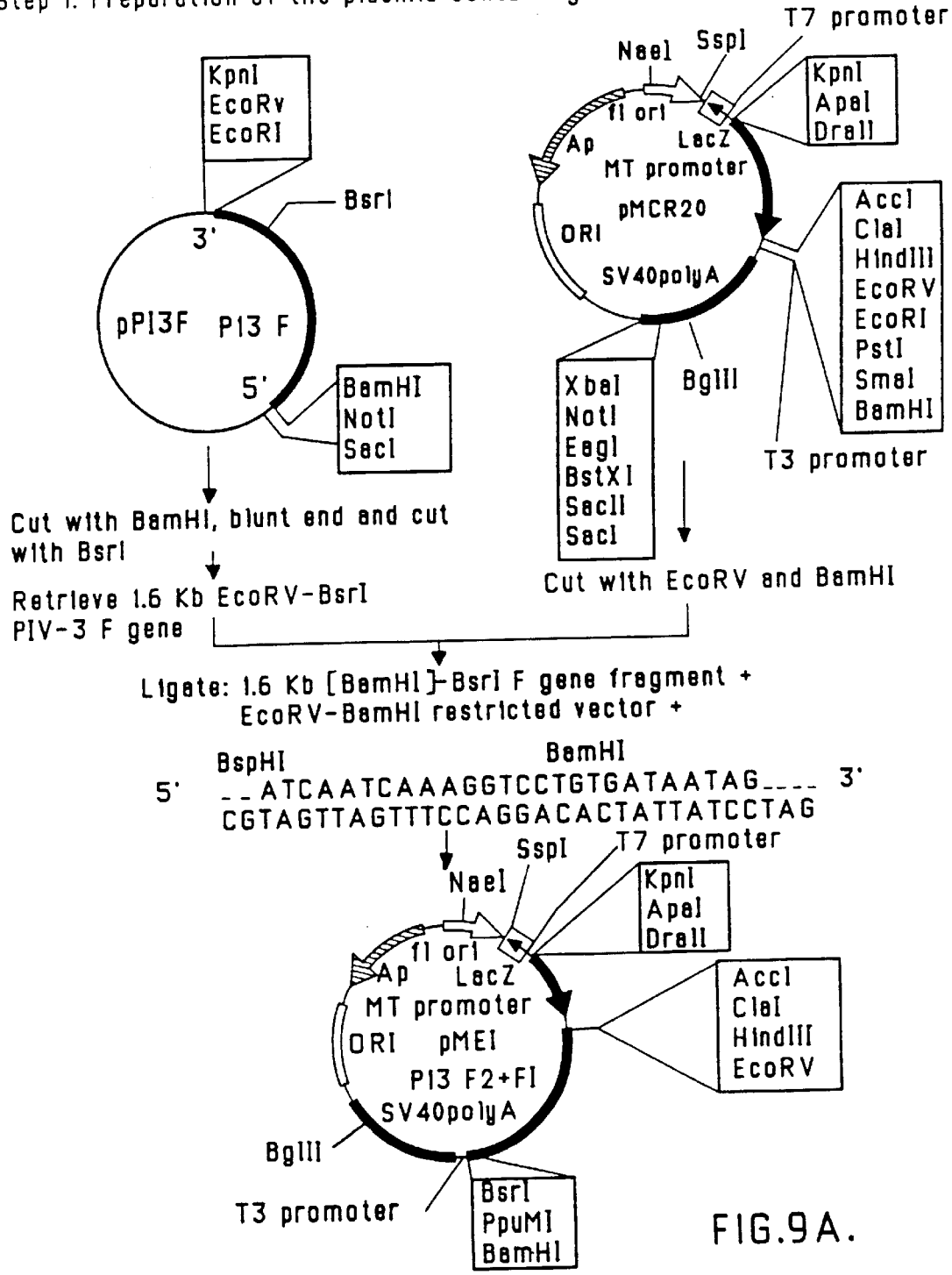

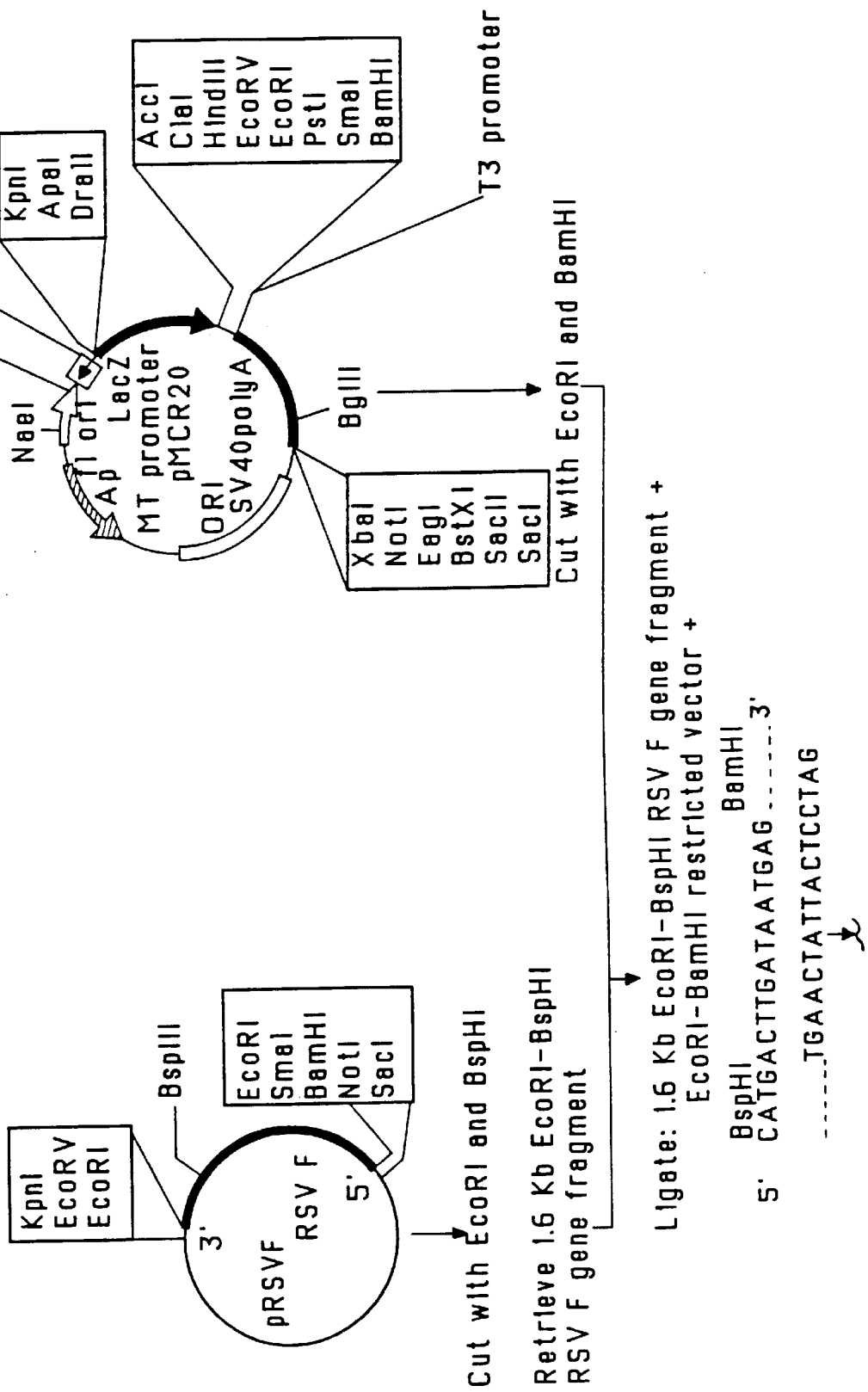
FIG.9B. Step 2: Preparation of the plasmid containing the modified RSV F gene

FIG.10B.

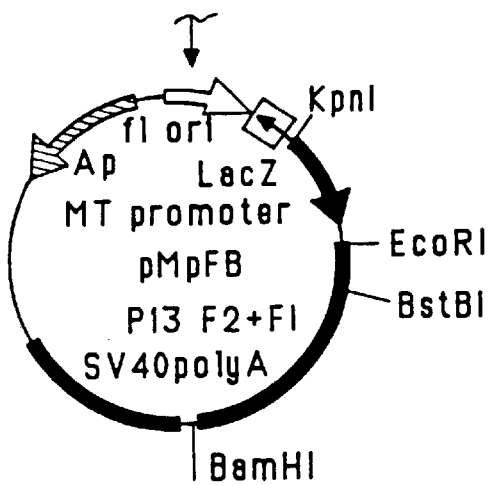

Cut with EcoRI and BstBI

Retreive: EcoRI-BstBI restricted vector

Ligate: EcoRI-BstBI restricted vector +

EcoRI                                                          PpuMI
AATTCATGCCAACTTTAATACTGCTAATTATTACAACAATGATTATGG
CATCTTCCTGCCAAATAGATATCACAAAACTACAGCAATGTAGGTGTA
TTGGTCAACAGTCCCAAAGGGATGAAGATATCACAAAACTT____ 3'
____GTACGGTTGAAATTATGACGATTAATAATGTTGTTACTAATACC
GTAGAAGGACGGTTTATCTATAGTGTTTTGATGTCGTACATCCACATA
ACCAGTTGTCAGGGTTTCCCTACTTCTATAGTGTTTTGAAGCTT

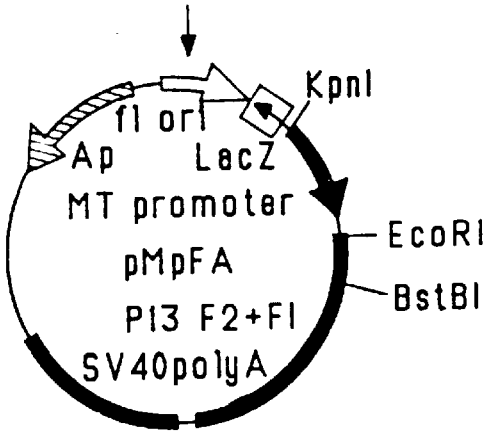

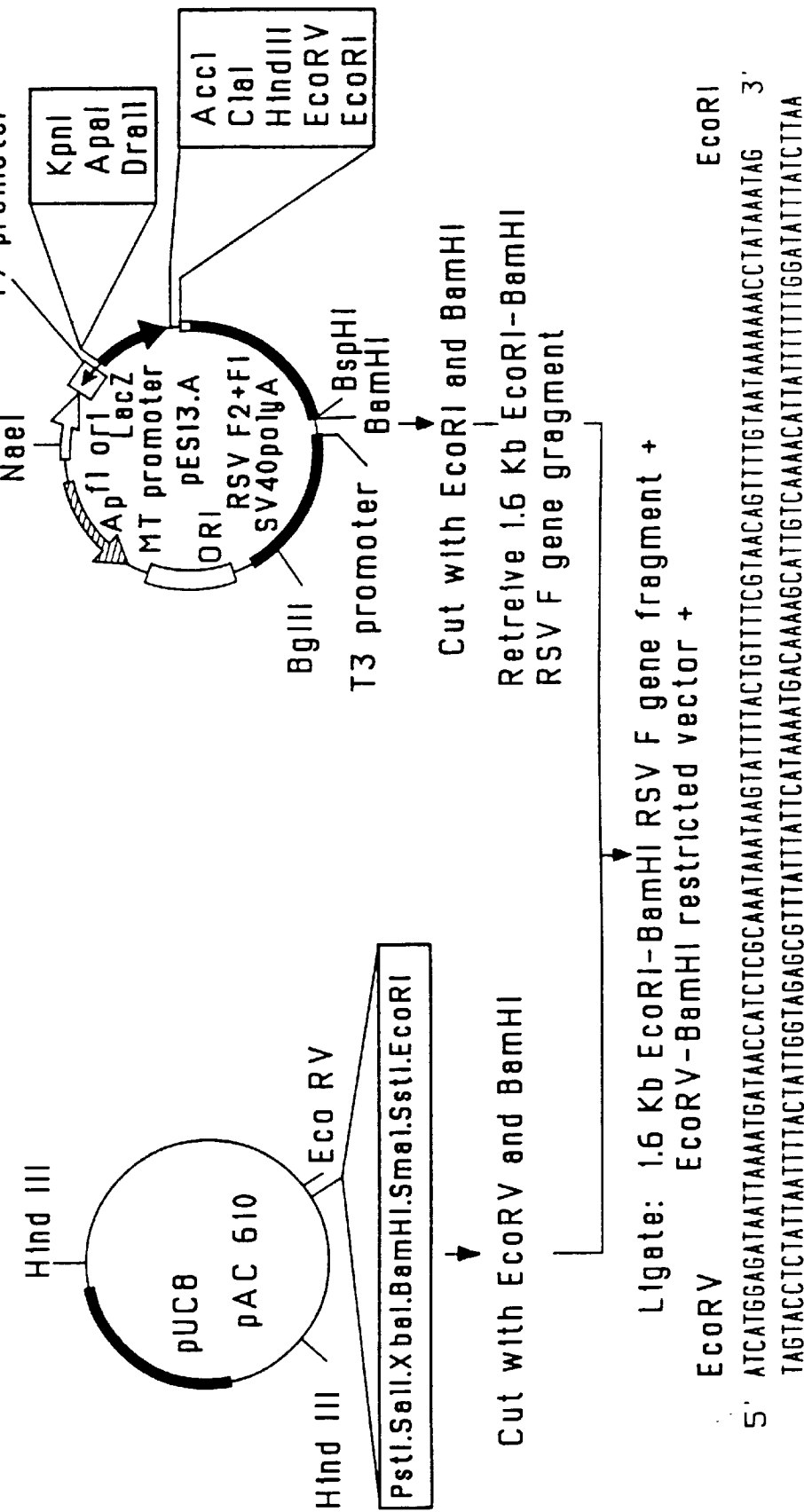
FIG. 12A. Construction of the modified pAc 610 baculovirus expression vector containing the chimeric $F_{PIV-3}$-$F_{RSV}$ gene consisting of the PIV-3 F gene lacking both the 5' untranslated sequence as well as the transmembrane and cytoplasmic tail coding regions linked to the truncated RSV F1 gene

FIG.13
IMMUNOBLOTS OF CELL LYSATES FROM Sf9 CELLS INFECTED WITH RECOMBINANT BACULOVIRUSES

| 1 | 2 | 3 |
|---|---|---|
| RSV F2+1 | $F_{PIV-3}-F_{RSV}$ | WILD TYPE |

A

| 1 | 2 | 3 |
|---|---|---|
| RSV F2+1 | $F_{PIV-3}-F_{RSV}$ | WILD TYPE |

B

FIG 13 : Immunoblots of cell lysates from Sf9 cells infected wirth recombinant baculoviruses containing the truncated RSV F gene ( Lane 1), the chimeric $F_{PIV-3}-F_{RSV}$ gene (Lane 2) or infected with wild type virus ( Lane 3) reacted with anti-F RSV Mab (panel A) and anti-F1 PIV-3 antiserum (panel B)

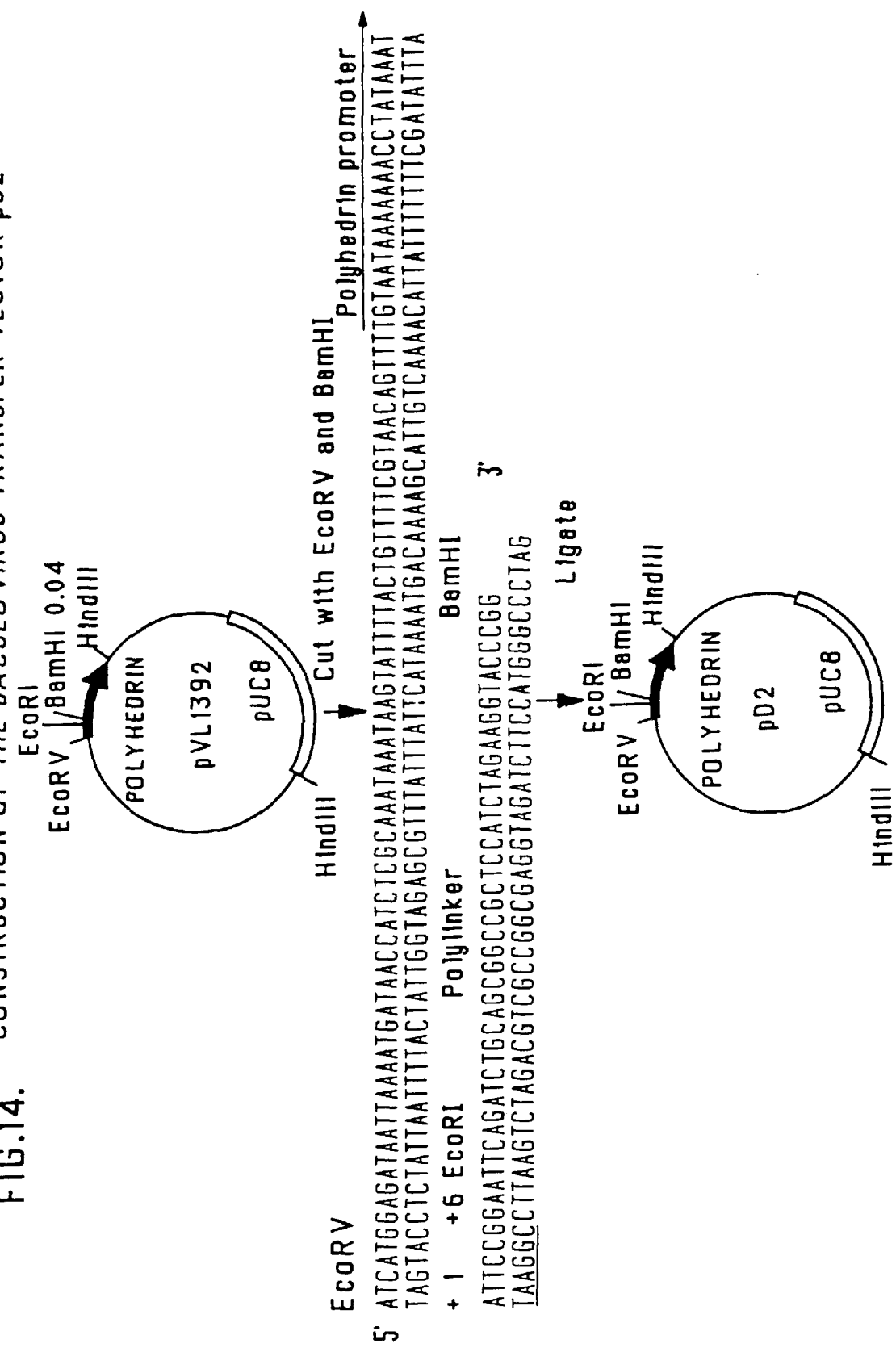
FIG.14. CONSTRUCTION OF THE BACULOVIRUS TRANSFER VECTOR pD2

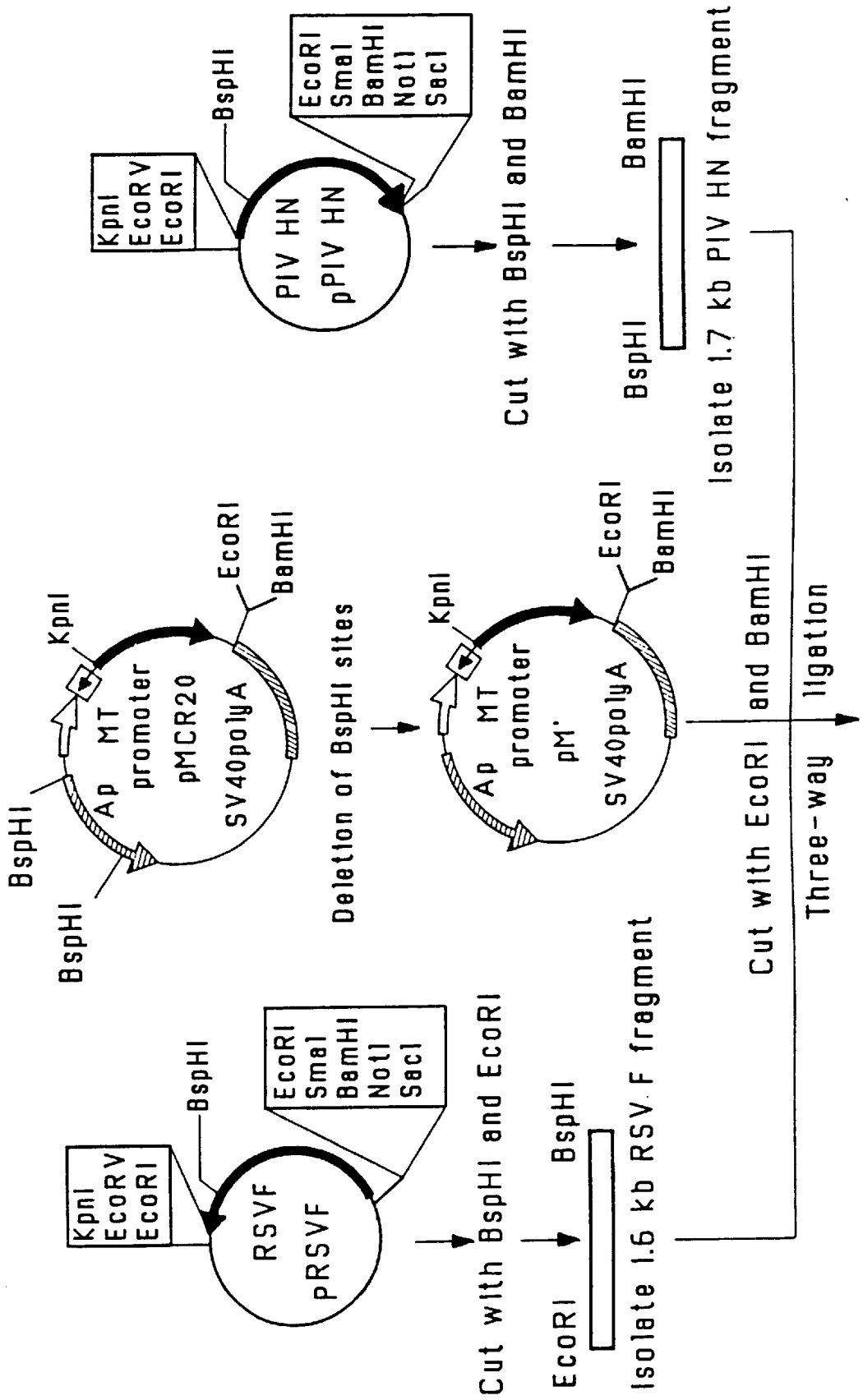
FIG.15A. CONSTRUCTION OF THE $F_{RSV}$-$HN_{PIV3}$ CHIMERIC GENE

FIG.16
SDS POLY ACRYLAMIDE GEL AND IMMUNOBLOTS OF PURIFIED $F_{RSV}$-$HN_{PIV-3}$ CHIMERIC PROTEIN

FIG 16 : A) Coomassie-stained SDS polyacrylamide gel of immunoaffinity- purified $F_{RSV}$-$HN_{PIV-3}$ protein.

B) Immunoblots of $F_{RSV}$-$HN_{PIV-3}$ protein reacted with an anti-F RSV Mab ( lane 1 ) and anti-HN PIV-3 antiserum ( lane 2)

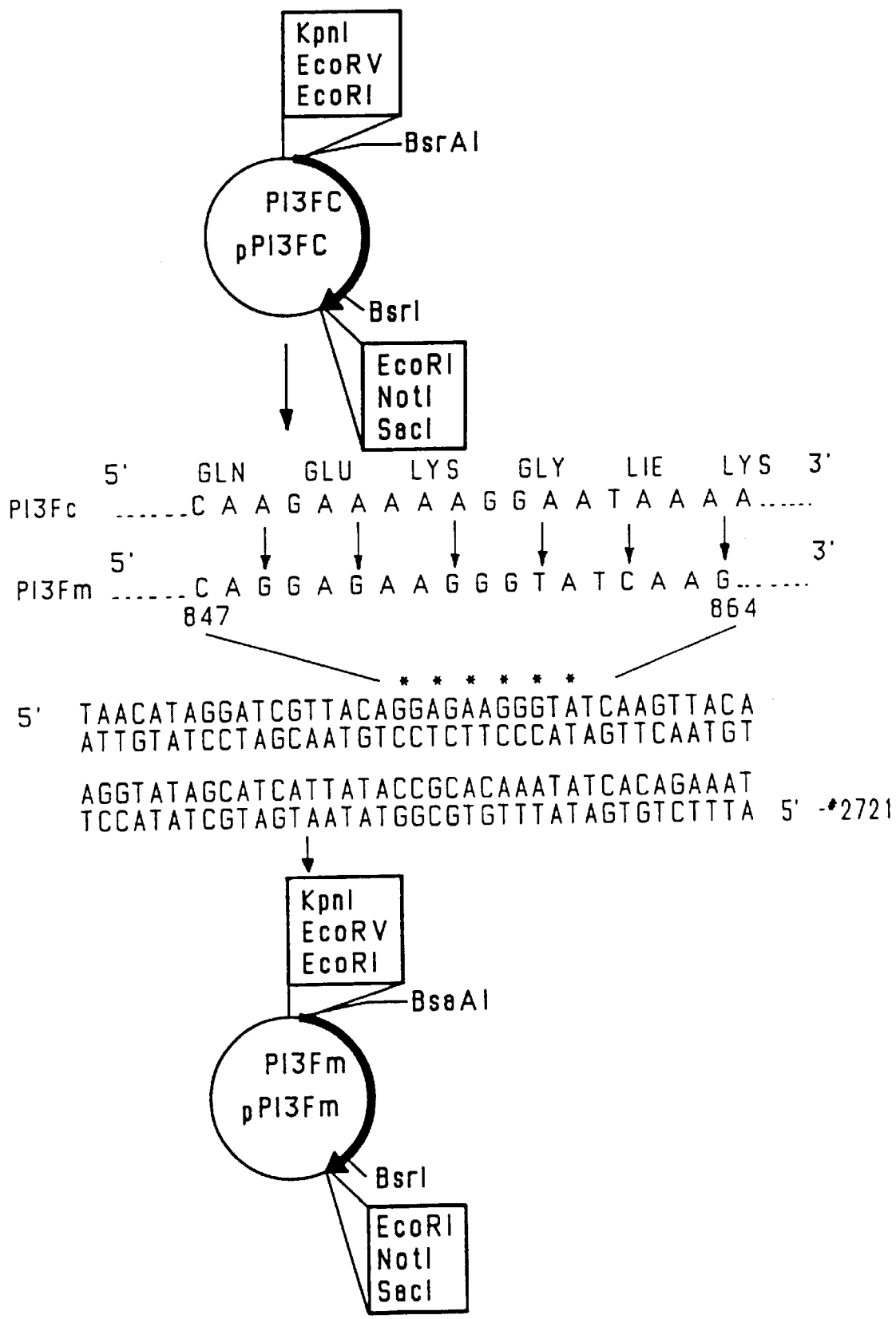
FIG. 17. MUTAGENESIS OF THE PIV-3 F GENE

FIG. 18. CONSTRUCTION OF THE $F_{PIV3}$-$G_{RSV}$ CHIMERIC GENE

MULTIMERIC HYBRID GENE ENCODING A CHIMERIC PROTEIN WHICH CONFERS PROTECTION AGAINST PARAINFLUENZA VIRUS AND RESPIRATORY SYNCTIAL VIRUS

FIELD OF INVENTION

The present invention relates to the engineering and expression of multimeric hybrid genes containing sequences from the gene coding for immunogenic proteins or protein fragments of numerous pathogens.

BACKGROUND TO THE INVENTION

The advantage of the approach taken by the present invention is to produce single immunogens containing protective antigens from a range of pathogens. Such chimeras greatly simplify the development of combination vaccines, in particular, with the view ultimately to produce single dose multivalent vaccines. Multivalent vaccines are currently made by separately producing pathogens and/or their pertinent antigens and combining them in various formulations. This is a labour intensive, costly and complex manufacturing procedure. In contrast, the availability of a single immunogen capable of protecting against a range of diseases would solve many of the problems of multivalent vaccine production. Several chimeric immunogens of the type provided herein may be combined to decrease the number of individual antigens required in a multivalent vaccine.

Human Parainfluenza virus types 1,2,3 and Respiratory syncytial virus types A and B are the major viral pathogens responsible for causing severe respiratory tract infections in infants and young children. It is estimated that, in the United States alone, approximately 1.6 million infants under one year of age will have a clinically significant RSV infection each year and an additional 1.4 million infants will be infected with PIV-3. Approximately 4000 infants less than one year of age in the United States die each year from complications arising from severe respiratory tract disease caused by infection with RSV and PIV-3. The WHO and NIALD vaccine advisory committees ranked RSV number two behind HIV for vaccine development while the preparation of an efficacious PIV-3 vaccine is ranked in the top ten vaccines considered a priority for vaccine development.

Safe and effective vaccines for protecting infants against these viral infections are not available and are urgently required. Clinical trials have shown that formaldehyde-inactivated and live-attenuated viral vaccines failed to adequately protect vaccinees against these infections. In fact, infants who received the formalin-inactivated RSV vaccine developed more serious lower respiratory tract disease during subsequent natural RSV infection than did the control group. [Am. J. Epidemiology 89, 1969, p. 405–421; J. Inf. Dis. 145, 1982, p. 311–319]. Furthermore, RSV glycoproteins purified by immunoaffinity chromatography using elution at acid pH induced immunopotentiation in cotton rats. [Vaccine, 10(7), 1992, p. 475–484]. The development of efficacious PIV-3 and RSV vaccines which do not cause exacerbated pulmonary disease in vaccinees following injection with wild-type virus would have significant therapeutic implications. It is anticipated that the development of a single recombinant immunogen capable of simultaneously protecting infants against diseases caused by infection with both Parainfluenza and Respiratory syncytial viruses could significantly reduce the morbidity and mortality caused by these viral infections.

It has been reported that a protective response against PIV-3 and RSV is contingent on the induction of neutralizing antibodies against the major viral surface glycoproteins. For PIV, these protective immunogens are the HN protein which has a molecular weight of 72 kDa and possesses both hemagglutination and neuraminidase activities and the fusion (F) protein, which has a molecular weight of 65 kDa and which is responsible for both fusion of the virus to the host cell membrane and cell-to-cell spread of the virus. For RSV, the two major immunogenic proteins are the 80 to 90 kDa G glycoprotein and the 70 kDa fusion (F) protein. The G and F proteins are thought to be functionally analogous to the PIV HN and F proteins, respectively. The PIV and RSV F glycoproteins are synthesized as inactive precursors (FO) which are proteolytically cleaved into N-terminal F2 and C-terminal F1 fragments which remain linked by disulphide bonds.

Recombinant surface glycoproteins from PIV and RSV have been individually expressed in insect cells using the baculovirus system [Ray et al., (1989), Virus Research, 12:169–180; Coelingh et al., (1987), Virology, 160:465–472; Wathen et al., (1989), J. of Inf. Dis. 159:253–263] as well as in mammalian cells infected with recombinant poxviruses [Spriggs, et al., (1987), J. Virol. 61:3416–3423; Stott et al., (1987), J. Virol. 61:3855–3861]. Recombinant antigens produced in these systems were found to protect immunized cotton rats against live virus challenge. More recently, hybrid RSV F-G [Wathan et al., (1989), J. Gen Virol. 70:2625–2635; Wathen, published International Patent application WO 89/05823] and PIV-3 F-HN [Wathen, published International Patent Application WO 89/10405], recombinant antigens have been engineered and produced in mammalian and insect cells. The RSV F-G hybrid antigen was shown to be protective in cotton rats [Wathan et al., (1989), J. Gen. Virol. 70:2637–2644] although it elicited a poor anti-G antibody response [Connors et al., (1992), Vaccine 10:475–484]. The protective ability of the PIV-3 F-HN protein was not reported in the published patent application. These antigens were engineered with the aim to protect against only the homologous virus, that is either RSV or PIV-3. However, it would be advantageous and economical to engineer and produce a single recombinant immunogen containing at least one protective antigen from each virus in order simultaneously to protect infants and young children against both PIV and RSV infections. The chimeric proteins provided herein for such purpose also may be administered to pregnant women or women of child bearing age to stimulate maternal antibodies to both PIV and RSV. In addition, the vaccine also may be administered to other susceptible individuals, such as the elderly.

SUMMARY OF INVENTION

In its broadest aspect, the present invention provides a multimeric hybrid gene, comprising a gene sequence coding for an immunogenic region of a protein from a first pathogen linked to a gene sequence coding for an immunogenic region of a protein from a second pathogen and to a chimeric protein encoded by such multimeric hybrid gene. Such chimeric protein comprises an immunogenic region of a protein from a first pathogen linked to an immunogenic region of a protein from a second pathogen.

The first and second pathogens are selected from bacterial and viral pathogens and, in one embodiment, may both be viral pathogens. Preferably, the first and second pathogens are selected from those causing different respiratory tract diseases, which may be upper and lower respiratory tract diseases. In a preferred embodiment, the first pathogen is parainfluenza virus and the second pathogen is respiratory syncytial virus. The PIV protein particularly is selected from PIV-3 F and HN proteins and the RSV protein particularly is selected from RSV G and F proteins. Another aspect of the invention provides cells containing the multimeric hybrid gene for expression of a chimeric protein encoded by the gene. Such cells may be bacterial cells, mammalian cells, insect cells, yeast cells or fungal cells. Further, the present invention provides a live vector for antigen delivery containing the multimeric hybrid gene, which may be a viral vector or a bacterial vector, and a physiologically-acceptable carrier therefor. Such live vector may form the active component of a vaccine against diseases caused by multiple pathogenic infections. Such vaccine may be formulated to be administered in an injectable form, intranasally or orally.

In an additional aspect of the present invention, there is provided a process for the preparation of a chimeric protein, which comprises isolating a gene sequence coding for an immunogenic region of a protein from a first pathogen; isolating a gene sequence coding for an immunogenic region of a protein from a second pathogen; linking the gene sequences to form a multimeric hybrid gene; and expressing the multimeric hybrid gene in a cellular expression system. The first and second pathogens are selected from bacterial and viral pathogens. Such cellular expression system may be provided by bacterial cells, mammalian cells, insect cells, yeast cells or fungal cells. The chimeric protein product of gene expression may be separated from a culture of the cellular expression system and purified.

The present invention further includes a vaccine against diseases caused by multiple pathogen infections, comprising the chimeric protein encoded by the multimeric hybrid gene and a physiologically-acceptable carrier therefor. Such vaccine may be formulated to be administered in an injectable form, intranasally or orally.

The vaccines provided herein may be used to immunize a host against disease caused by multiple pathogenic infections, particularly those caused by a parainfluenza virus and respiratory syncytial virus, by administering an effective amount of the vaccine to the host. As noted above, for human PIV and RSV, the host may be infants and young children, pregnant women as well as those of a child-bearing age, and other susceptible persons, such as the elderly.

The chimeric protein provided herein also may be used as a diagnostic reagent for detecting infection by a plurality of different pathogens in a host, using a suitable assaying procedure.

It will be appreciated that, while the description of the present invention which follows focuses mainly on a chimeric molecule which is effective for immunization against diseases caused by infection by PIV and RSV, nevertheless the invention provided herein broadly extends to any chimeric protein which is effected for immunization against diseases caused by a plurality of pathogens, comprising an antigen from each of the pathogens linked in a single molecule, as well as to genes coding for such chimeric molecules.

In this application, by the term "multimeric hybrid genes" we mean genes encoding antigenic regions of proteins from different pathogens and by the term "chimeric proteins" we mean immunogens containing antigenic regions from proteins from different pathogens.

BRIEF DESCRIPTION OF DRAWINGS

FIG. 1 shows the nucleotide (SEQ ID No:1) and amino acid (SEQ ID No:2) sequence of a PCR-amplified PIV-3 F gene and F protein, respectively;

FIG. 3 shows the nucleotide (SEQ ID No:3) and amino acid (SEQ ID No:4) sequences of the PIV-3 HN gene and HN protein, respectively;

FIG. 5 shows the nucleotide (SEQ ID No:5) and amino acid (SEQ ID No:6) sequences of the RSV F gene and RSV F protein, respectively;

FIG. 7 shows the nucleotide (SEQ ID No:7) and amino acid (SEQ ID No:8) sequences of the RSV G gene and RSV G protein, respectively;

FIG. 8 shows the restriction map of the RSV G gene;

FIGS. 13A and 13B show immunoblots of cell lysates from Sf9 cells infected with recombinant baculoviruses;

FIG. 14 shows the steps involved in constructing a baculovirus transfer vector (pD2);

FIGS. 16A and 16B show an SDS-PAGE gel and immunoblot of purified $F_{RSV}$-$HN_{PIV-3}$ chimeric protein;

FIG. 17 illustrates mutagenesis of a PIV-3 F gene; and

FIG. 18 shows the steps involved in the construction of a chimeric $F_{PIV-3}$-$G_{RSV}$ gene.

GENERAL DESCRIPTION OF INVENTION

Figure 2:
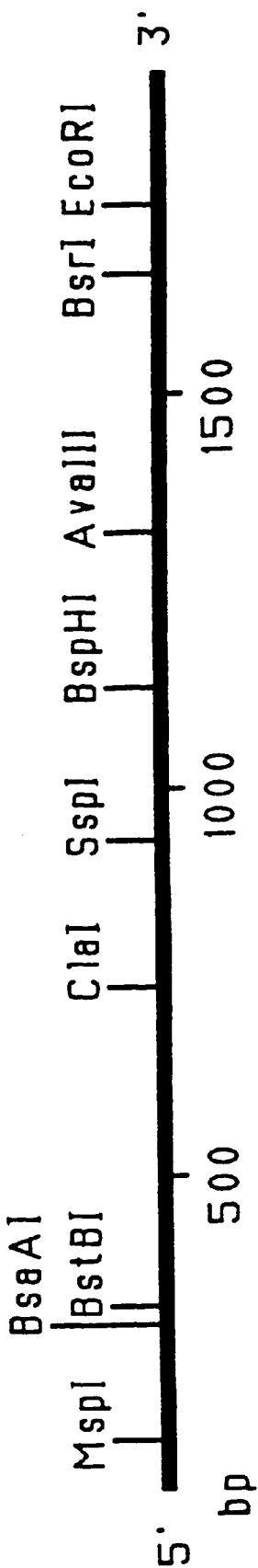
FIG. 2 shows the restriction map of the PIV-3 F gene.

In the present invention, a chimeric molecule protective against two different major childhood diseases is provided. The present invention specifically relates to the formulation of various recombinant Parainfluenza virus (PIV)/ Respiratory syncytial virus (RSV) immunogens to produce safe and efficacious vaccines capable of protecting infants and young children, as well as other susceptible individuals, against diseases caused by infection with both PIV and RSV. However, as described above, the present invention extends to the construction of multimeric hybrid genes containing genes coding for protective antigens from many pathogens. Such vaccines may be administered in any desired manner, such as a readily-injectable vaccine, intranasally or orally.

In the present invention, the inventors have specifically engineered several model PIV/RSV chimeric genes containing relevant sequences from selected genes coding for PIV-3 and RSV surface glycoproteins linked in tandem. All genes in the chimeric constructs described herein were obtained from recent clinical isolates of PIV-3 and RSV. The chimeric gene constructs may include gene sequences from either PIV-3 F or HN genes linked in tandem to either RSV F or G genes in all possible relative orientations and combinations.

The chimeric gene constructs provided herein may consist of either the entire gene sequences or gene segments coding for immunogenic and protective epitopes thereof. The natural nucleotide sequence of these genes may be modified by mutation while retaining antigenicity and such modifications may include the removal of putative pre-transcriptional terminators to optimize their expression in eukaryotic cells. The genes were designed to code for hybrid PIV-RSV surface glycoproteins linked in tandem in a single construct to produce gene products which elicit protective antibodies against both parainfluenza and respiratory syncytial viruses. Such multimeric hybrid genes consist of a gene sequence coding for a human PIV-3 F or HN protein or an immunogenic epitope-containing fragment thereof linked to a gene sequence coding for a human RSV G or F protein or an immunogenic epitope-containing fragment thereof. Specific gene constructs which may be employed include $F_{PIV-3}$-$F_{RSV}$, $F_{RSV}$-$HN_{PIV-3}$ and $F_{PIV-3}$ -$G_{RSV}$ hybrid genes.

In addition, the present invention also extends to the construction of other multimeric genes, such as trimeric genes containing PIV and RSV genes or gene segments, linked in all possible relative orientations. For example:

$F_{PIV}$-$HN_{PIV}$-F or $G_{RSV}$ $F_{PIV}$-$F_{RSV}$-$G_{RSV}$ $HN_{PIV}$-$F_{RSV}$-$G_{RSV}$

The multimeric genes provided herein also may comprise at least one gene encoding at least one immunogenic and/or immunostimulating molecule.

The multimeric hybrid genes provided herein may be sub-cloned into appropriate vectors for expression in cellular expression systems. Such cellular expression systems may include bacterial, mammalian, insect and fungal, such as yeast, cells.

The chimeric proteins provided herein also may be presented to the immune system by the use of a live vector, including live viral vectors, such as recombinant poxviruses, adenoviruses, retroviruses, Semliki Forest viruses, and live bacterial vectors, such as Salmonella and mycobacteria (e.g. BCG).

Chimeric proteins, such as a PIV/RSV chimera, present in either the supernatants or cell lysates of transfected, transformed or infected cells then can be purified in any convenient manner.

To evaluate the immunogenicity and protective ability of the chimeric proteins, suitable experimental animals are immunized with either varying doses of the purified chimeric proteins, such as the PIV/RSV chimera, and/or live recombinant vectors as described above. Such chimeric proteins may be presented to the immune system by either the use of physiologically-acceptable vehicles, such as aluminum phosphate, or by the use of delivery systems, such as ISCOMS and liposomes. The chimeras also may be formulated to be capable of eliciting a mucosal response, for example, by conjugation or association with immunotargeting vehicles, such as the cholera toxin B subunit, or by incorporation into microparticles. The vaccines may further comprise means for delivering the multimeric protein specifically to cells of the immune system, such as toxin molecules or antibodies. To further enhance the immunoprotective ability of the chimeric proteins, they may be supplemented with other immunogenic and/or immunostimulating molecules. The chimeric PIV/RSV proteins specifically described herein may be formulated with an adjuvant, such as aluminum phosphate, to produce readily-injectable vaccines for protection against the diseases caused by both PIV-3 and RSV. The chimeric proteins also may be administered intranasally or orally. The chimeric proteins may be used in test kits for diagnosis of infection by PIV-3 and RSV.

The invention is not limited to the preparation of chimeric PIV-3 and RSV proteins, but is applicable to the production of chimeric immunogens composed of either the entire sequences or regions of the immunogenic proteins from at least two pathogens sequentially linked in a single molecule. Chimeric antigens also may be synthesized to contain the immunodominant epitopes of several proteins from different pathogens. These chimeric antigens may be useful as vaccines or as diagnostic reagents.

SEQUENCE IDENTIFICATION

Figure 9C:
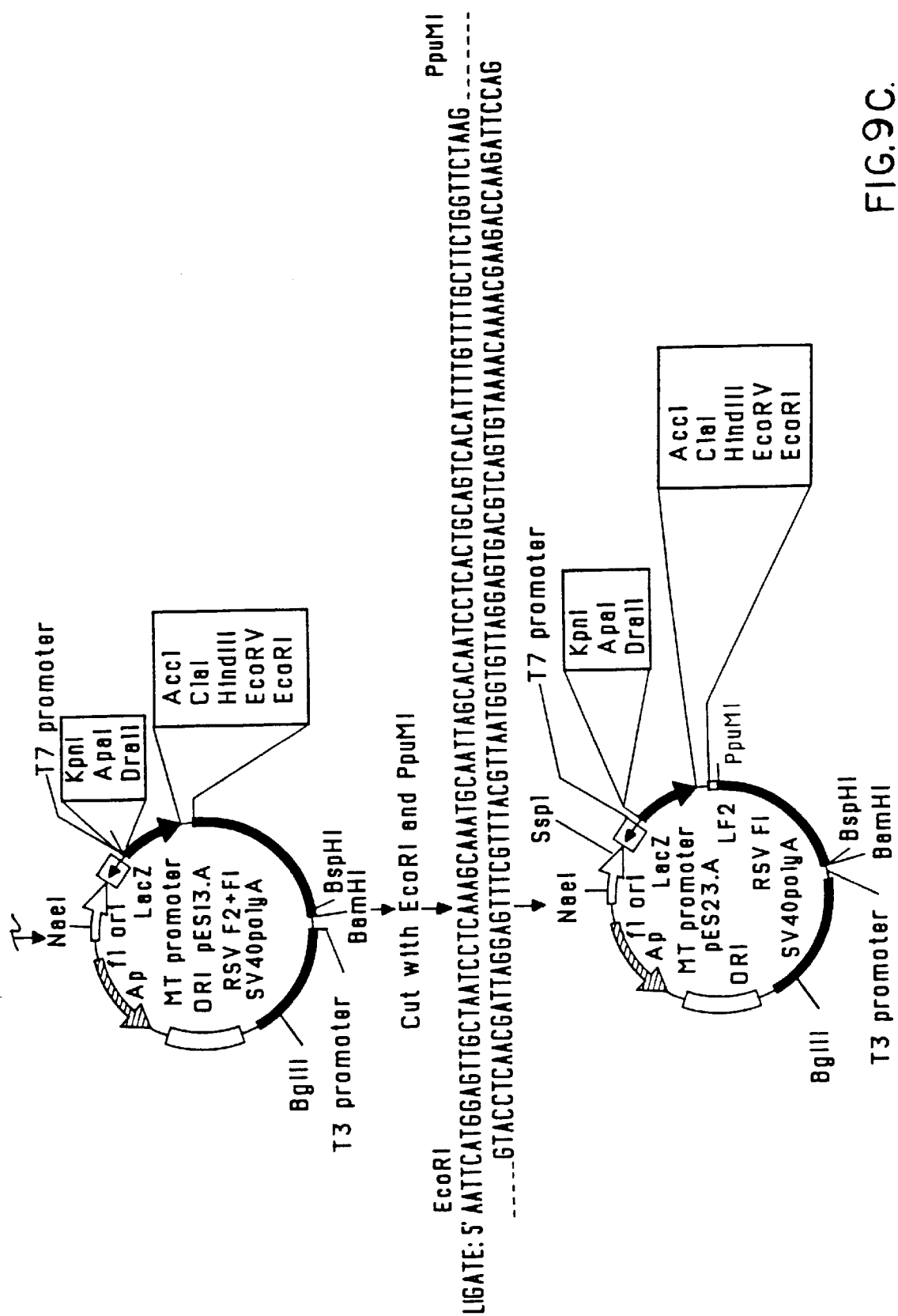
FIG. 9 shows the steps involved in the construction of an expression vector containing a chimeric $F_{PIV-3}$-$F_{RSV}$ gene.
Figure 9D:
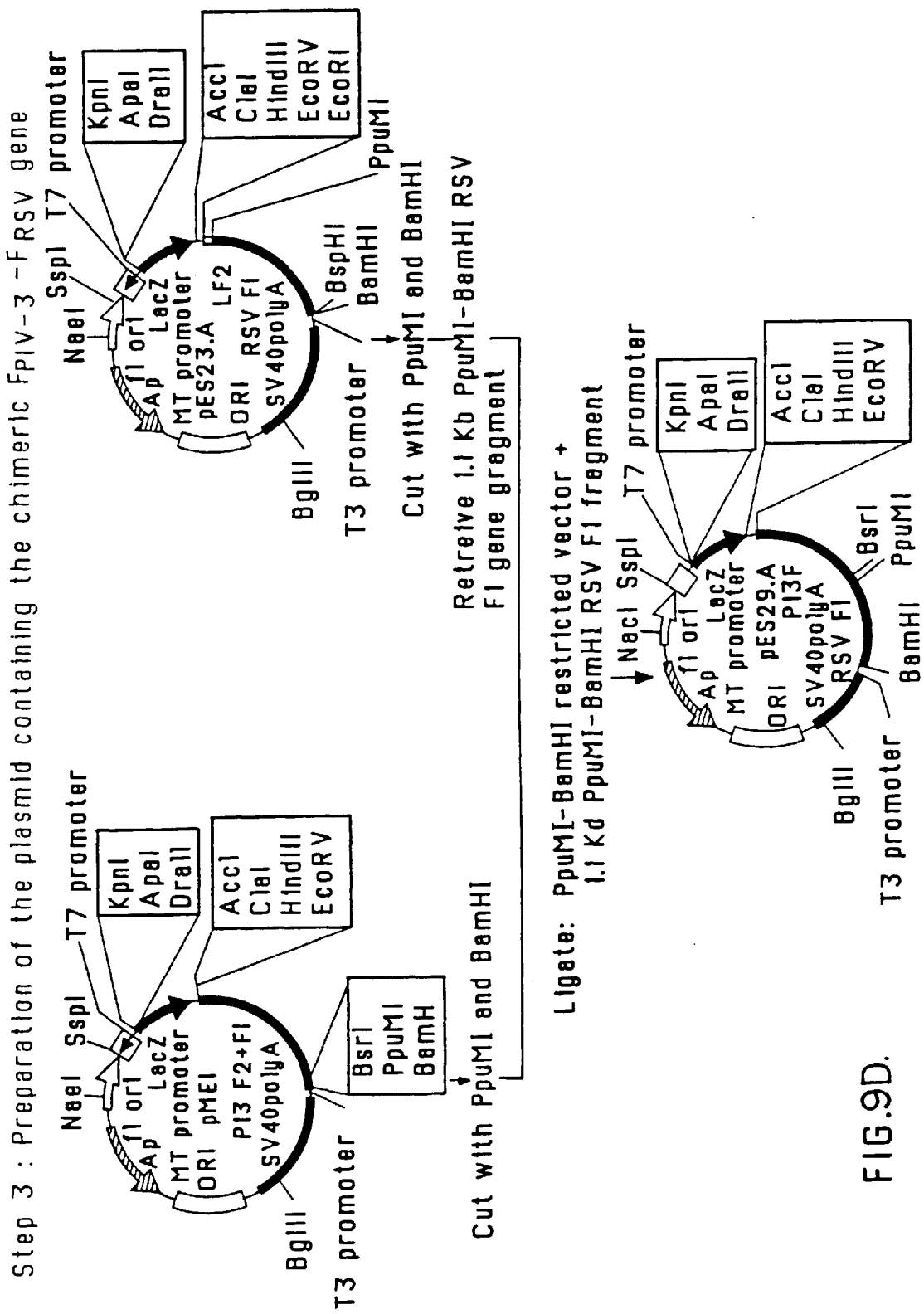
Figure 10A:
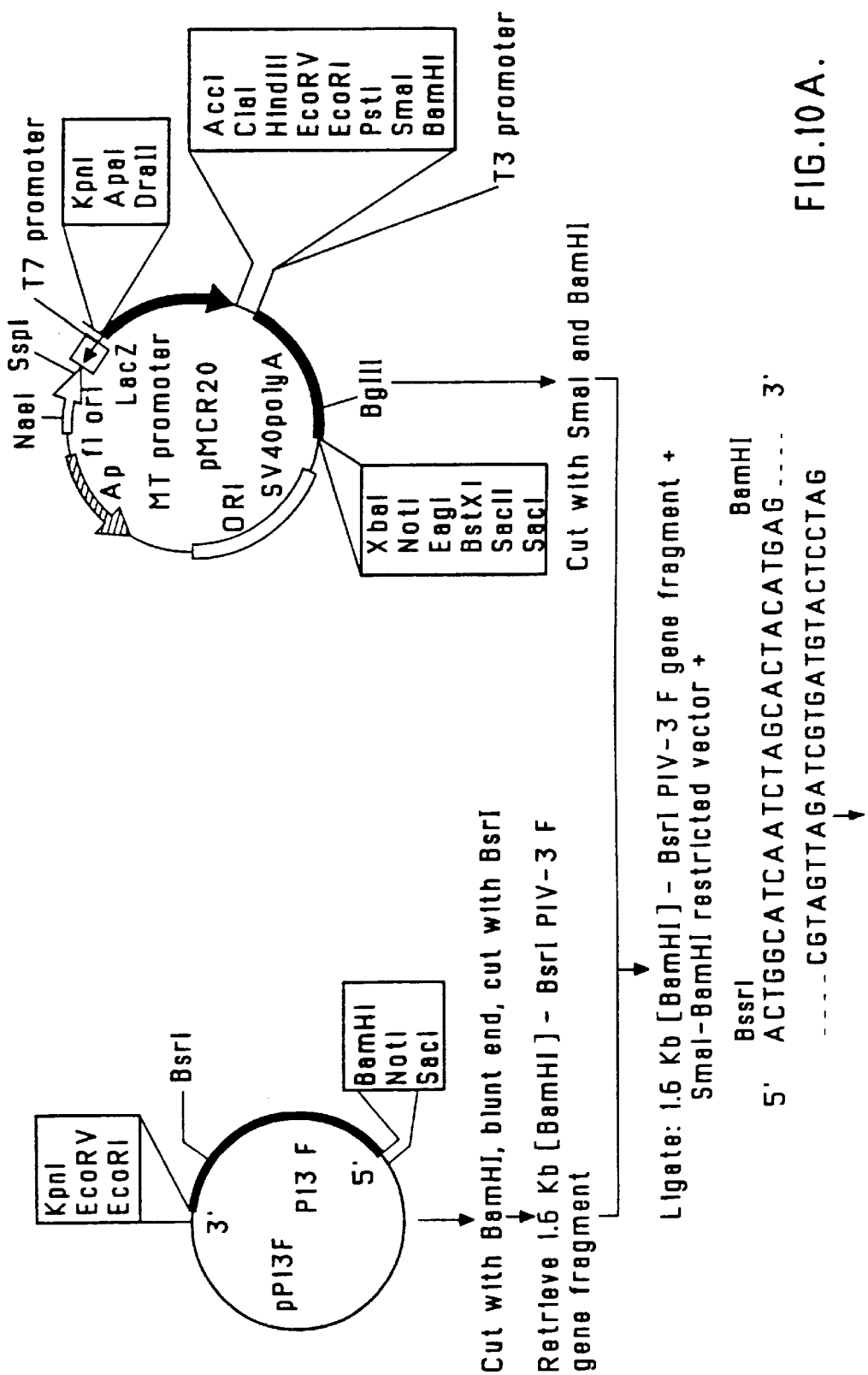
FIG. 10 shows the steps involved in the construction of an expression vector containing a $F_{PIV-3}$ gene lacking the 5'-untranslated sequence and transmembrane anchor and cytoplasmic tail coding regions.
Figure 11:
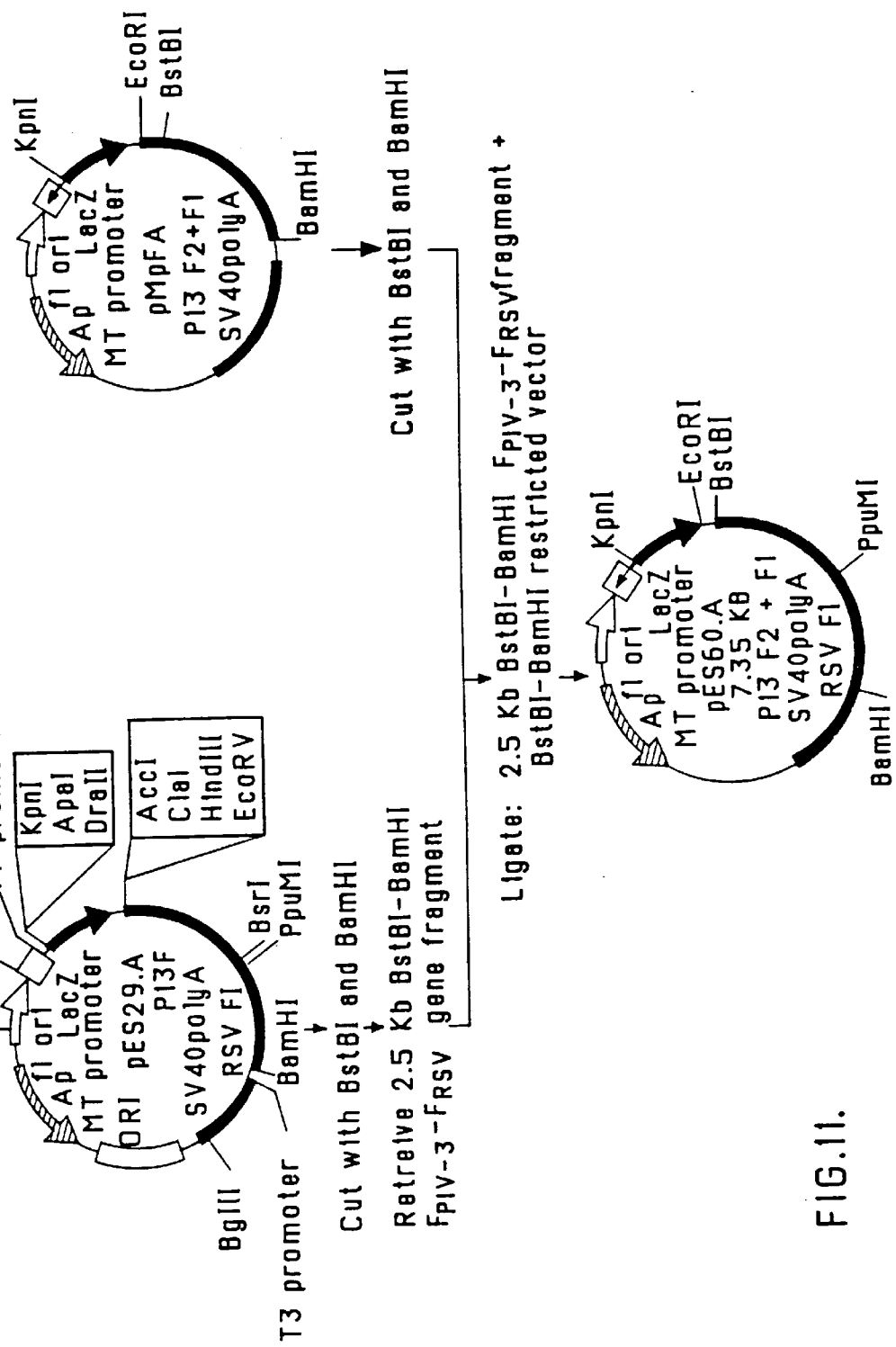
FIG. 11 shows the steps involved in the construction of an expression vector containing a chimeric $F_{PIV-3}$-$F_{RSV}$ gene containing a truncated PIV-3 F gene devoid of 5'-untranslated region linked to a truncated RSV F1 gene.
Figure 15B:
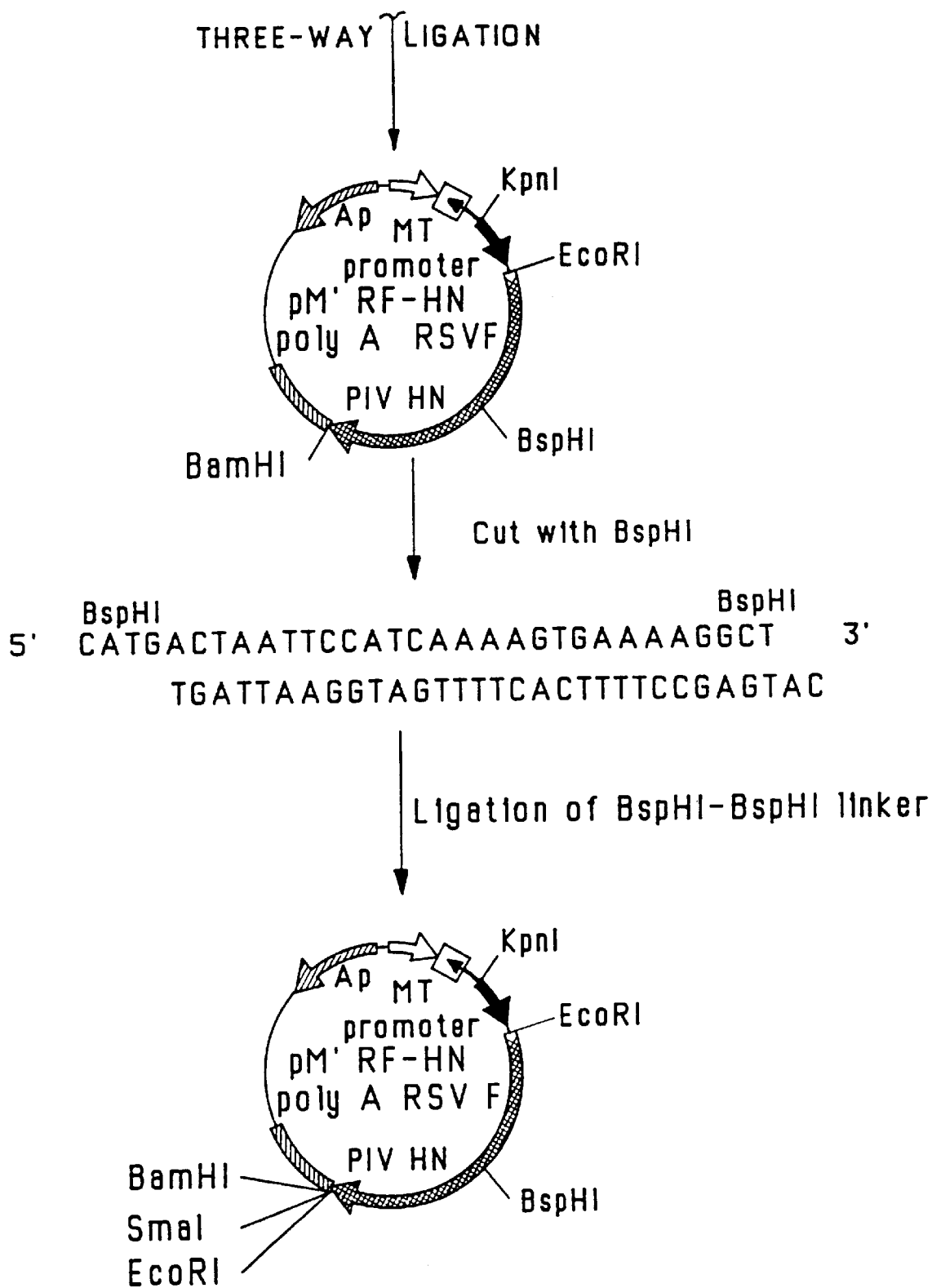
FIG. 15 shows the steps involved in construction of a chimeric $F_{RSV}$-$HN_{PIV-3}$ gene.

Several nucleotide and amino acid sequences are referred to in the disclosure of this application. The following table identifies the sequences and the location of the sequence:

| SEQ. ID No. | Identification | Location |
|---|---|---|
| 1 | Nucleotide sequence for PCR-amplified PIV-3 F gene | FIG. 1, Example 1 |
| 2 | Amino acid sequence for PCR-amplified PIV-F protein | FIG. 1, Example 1 |
| 3 | Nucleotide sequence for PIV-3 HN gene | FIG. 3, Example 1 |
| 4 | Amino acid sequence for PIV-3 HN protein | FIG. 3, Example 1 |
| 5 | Nucleotide sequence for RSV F gene | FIG. 5, Example 1 |
| 6 | Amino acid sequence for RSV F protein | FIG. 5, Example 1 |
| 7 | Nucleotide sequence for RSV G gene | FIG. 7, Example 1 |
| 8 | Amino acid sequence for RSV G protein | FIG. 7, Example 1 |
| 9 | BsrI - BamHI oligo-nucleotide cassette | FIG. 9, Example 2 |
| 10 | BspHI - BamHI oligo-nucleotide cassette | FIG. 9, Example 2 |
| 11 | EcoRI - Ppu MI oligo-nucleotide cassette | FIG. 9, Example 2 |
| 12 | BrsI - BamHI oligo-nucleotide cassette | FIG. 10, Example 3 |
| 13 | EcoRI -Bsr BI oligo-nucleotide cassette | FIG. 10, Example 3 |
| 14 | EcoRV - EcoRI oligo-nucleotide cassette | FIG. 11, Example 5 |
| 15 | EcoRV - BamHI oligo-nucleotide cassette | FIG. 14, Example 8 |
| 16 | BspHI - BspHI oligo-nucleotide cassette | FIG. 15, Example 9 |
| 17 | Nucleotide sequence for PIV-3 F gene | Example 15 |
| 18 | Mutagenic oligo-nucleotide #2721 | FIG. 17, Example 15 |
| 19 | Nucleotide sequence for part of oligo-nucleotide #2721 | Example 15 |
| 20 | Oligonucleotide probe | Example 15 |

DEPOSIT INFORMATION

Certain plasmid DNAs described and referred to herein have been deposited with the American Type Culture Collection (ATCC) located at 10801 University Boulevard, Manassas, Va. 20110-2209, USA, pursuant to the Budapest Treaty and prior to the filing of this application. The deposited purified plasmids will become available to the public and all restrictions imposed on access to the deposits will be removed upon grant of this U.S. patent application or upon publication of its corresponding European patent application, whichever first occurs. The invention described and claimed herein is not to be limited in scope by the plasmid DNAs of the constructs deposited, since the deposited embodiment is intended only as an illustration of the invention. The following purified plasmids were deposited at the ATCC with the noted accession numbers on Dec. 17, 1992:

| Plasmid | Example No. | Accession No. |
| --- | --- | --- |
| pAC DR7 | 5 | 75387 |
| pD2RF-HN | 9 | 75388 |
| pD2F-G | 16 | 75389 |

Any equivalent plasmids that can be used to produce equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods for cloning and sequencing the PIV-3 and RSV genes as well as the procedures for sub-cloning the genes into appropriate vectors and expressing the gene constructs in mammalian and insect cells are not explicitly described in this disclosure but are well within the scope of those skilled in the art.

Example 1

This Example outlines the strategy used to clone and sequence the PIV-3 F, HN and RSV F, G genes (from a type A isolate). These genes were used in the construction of the $F_{PIV-3}$-$F_{RSV}$, $F_{RSV}$-$HN_{PIV-3}$, and $F_{PIV-3}$-$G_{RSV}$ chimeric genes detailed in Examples 2 to 4, 9 and 15, respectively.

Two PIV-3 F gene clones initially were obtained by PCR amplification of cDNA derived from viral RNA extracted from a recent clinical isolate of PIV-3. Two other PIV-3 F gene clones as well as the PIV-3 HN, RSV F and RSV G genes were cloned from a cDNA library prepared from mRNA isolated from MRC-5 cells infected with clinical isolates of either PIV-3 or RSV (type A isolate). The PIV-3 F (both PCR amplified and non-PCR amplified), PIV-3 HN, RSV F and RSV G gene clones were sequenced by the dideoxynucleotide chain termination procedure. Sequencing of both strands of the genes was performed by a combination of manual and automated sequencing.

The nucleotide (SEQ ID No:1) and amino acid (SEQ ID No:2) sequences of the PCR amplified PIV-3 F gene and F protein, respectively, are presented in FIG. 1 and the restriction map of the gene is shown in FIG. 2. Sequence analysis of the 1844 nucleotides of two PCR amplified PIV-3 F gene clones confirmed that the clones were identical. Comparison of the coding sequence of the PCR-amplified PIV-3 F gene clone with that of the published PIV-3 F gene sequence revealed a 2.6% divergence in the coding sequence between the two genes resulting in fourteen amino acid substitutions.

The nucleotide sequence of the non-PCR amplified PIV-3 F gene clone differed from the PCR amplified gene clone in the following manner: the non-PCR amplified clone had ten additional nucleotides (AGGACAAAAG) (SEQ ID NO:21) 5' untranslated region of the gene and differed at four positions, 8 (T in PCR-amplified gene to C in non-PCR amplified gene), 512 (C in PCR-amplified gene to T in non-PCR amplified gene), 518 (G in PCR-amplified gene to A in non-PCR amplified gene) and 1376 (A in PCR-amplified gene to G in non-PCR amplified gene). These changes resulted in three changes in the amino acid sequence of the F protein encoded by the non-PCR amplified PIV-3 F gene. Serine (position 110), glycine (position 112), and aspartic acid (position 398) in the primary amino acid sequence of the F protein encoded by the PCR amplified PIV-3 F gene was changed to phenylalanine (position 110), glutamic acid (position 112) and glycine (position 398), respectively, in the primary amino acid sequence of the F protein encoded by the PCR amplified clone.

Figure 3B:
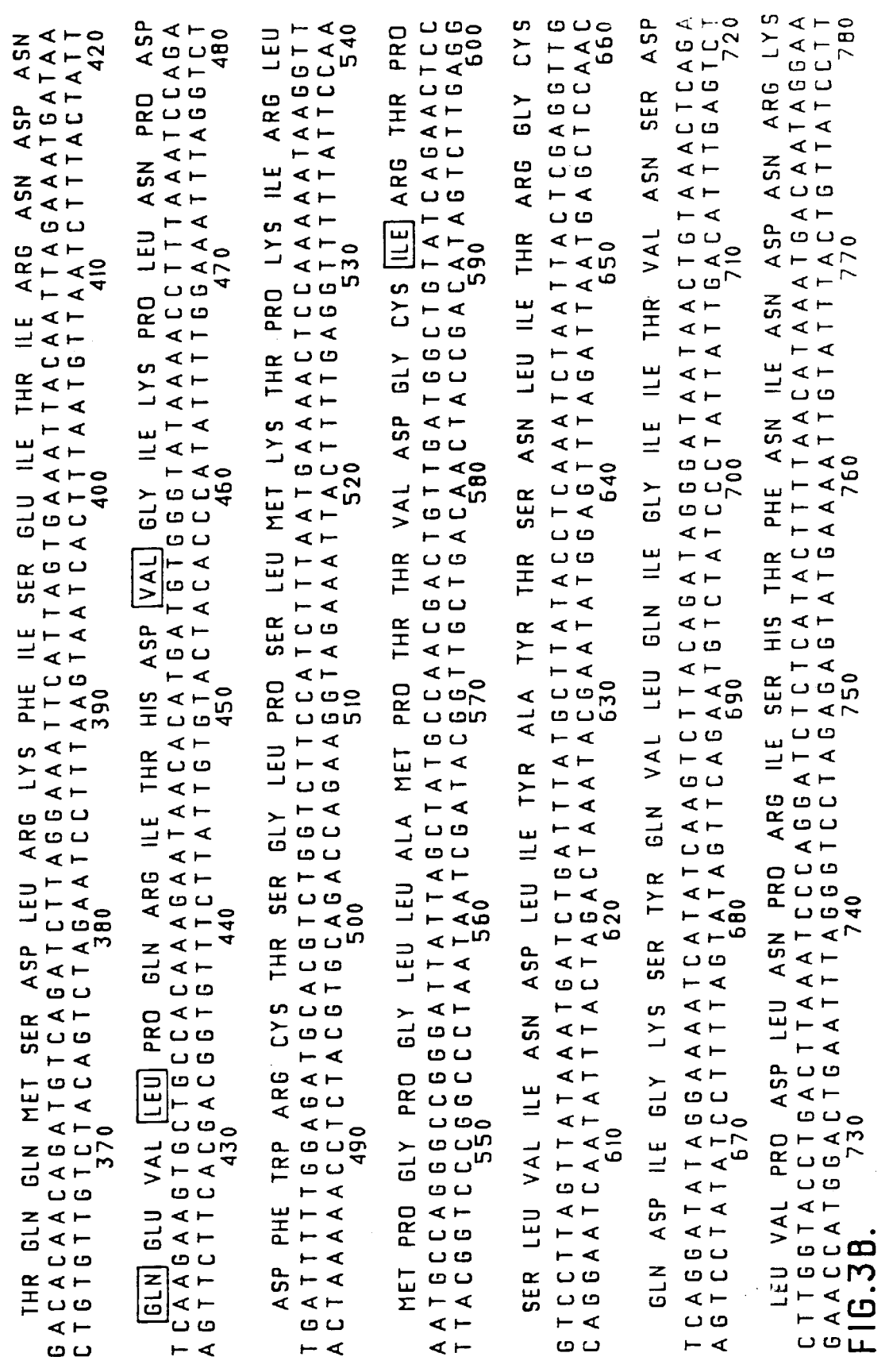
Figure 3C:
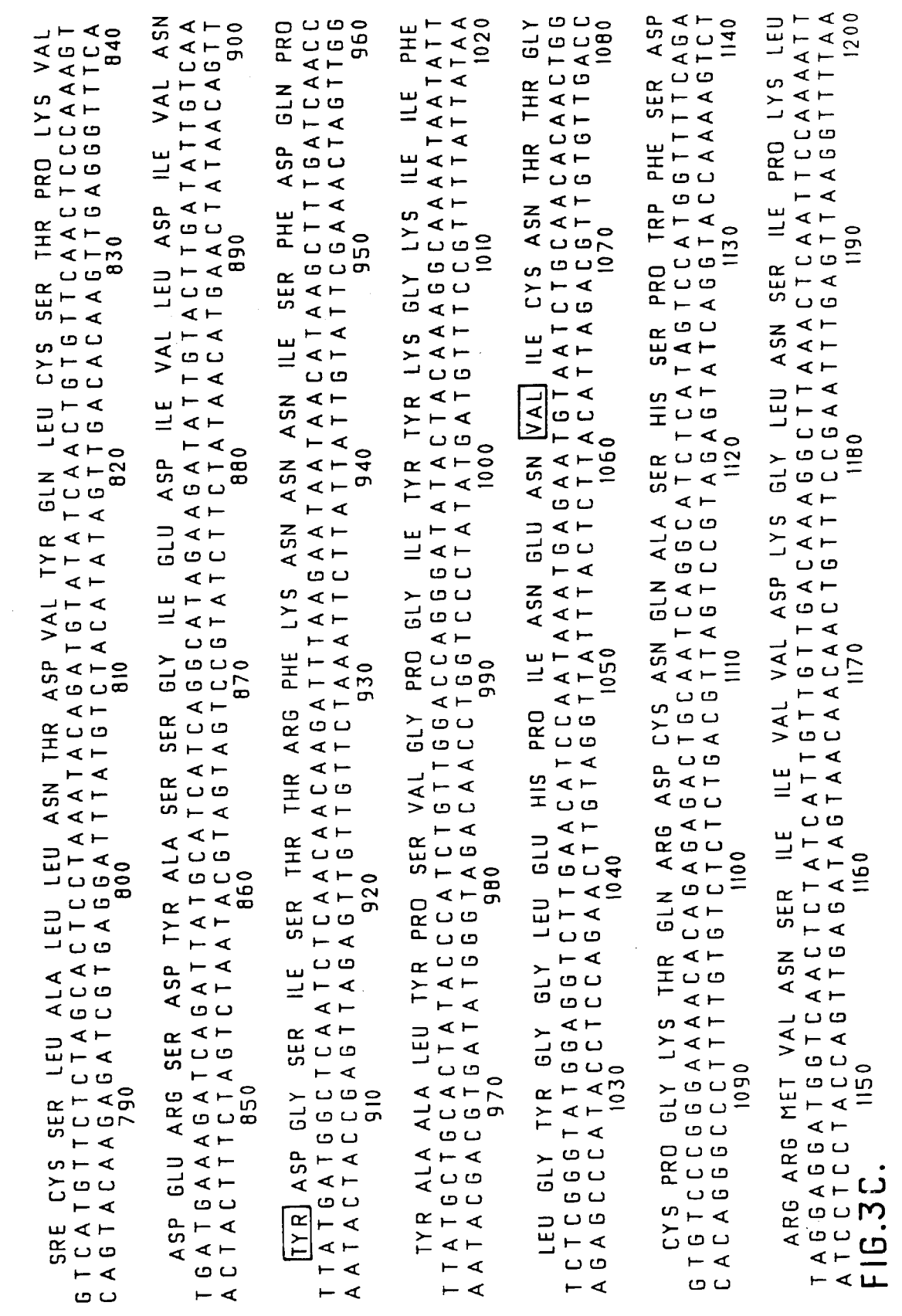
Figure 3D:
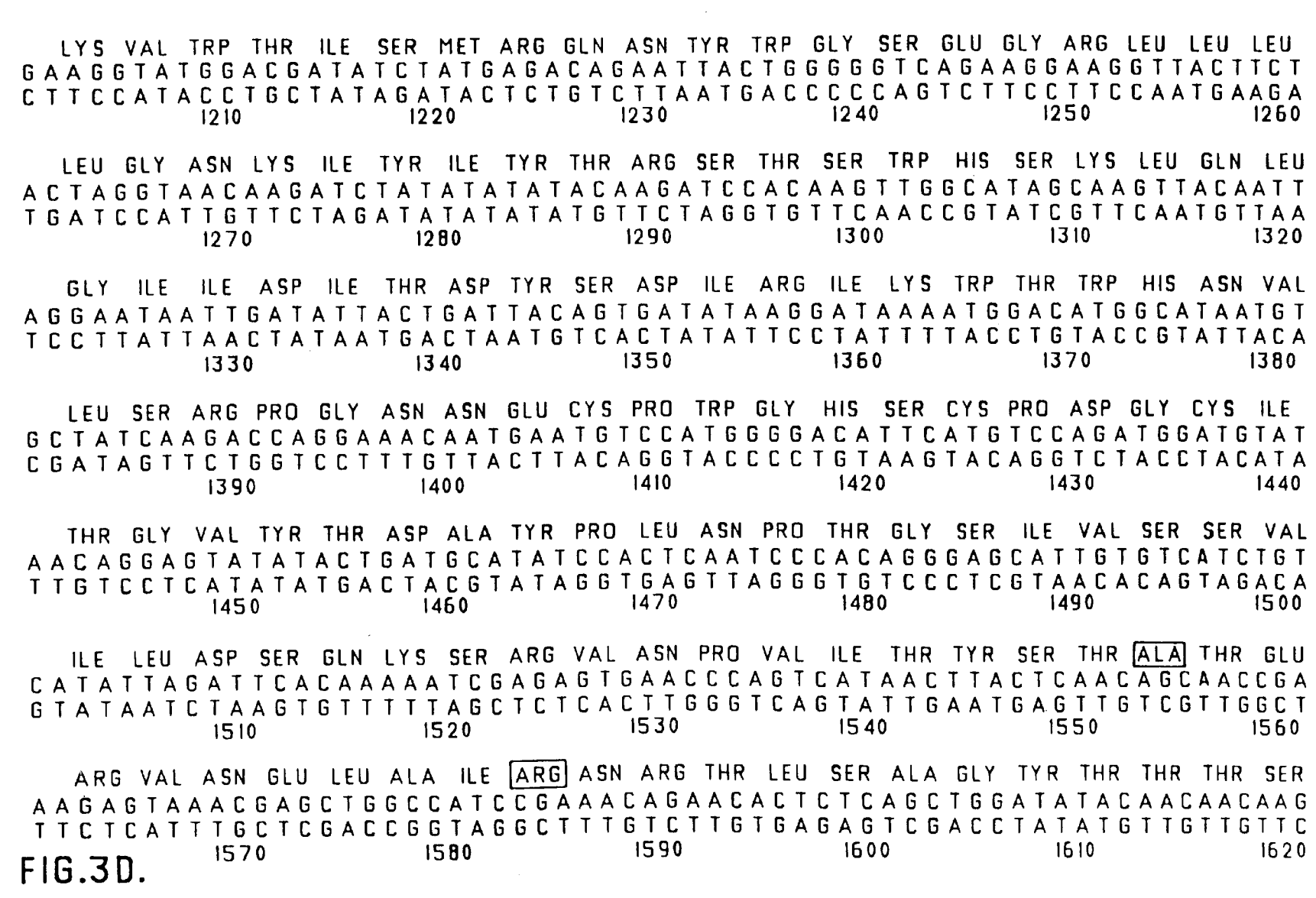
Figure 4:
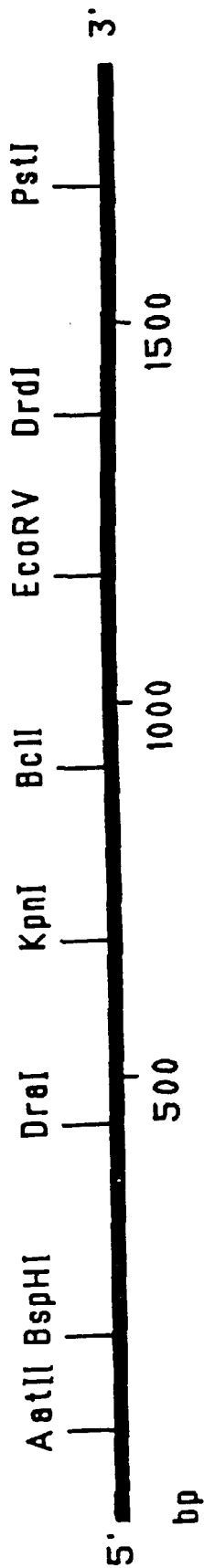
FIG. 4 shows the restriction map of the PIV-3 HN gene.

FIG. 3 shows the nucleotide (SEQ ID No:3) and amino acid (SEQ ID No:4) sequences of the PIV-3 HN gene and protein, respectively and the restriction map of the gene is presented in FIG. 4. Analysis of the 1833 nucleotide sequence from two HN clones confirmed that the sequences were identical. A 4.4% divergence in the coding sequence of the PIV-3 HN gene was noted when the sequence was compared to the published PIV-3 HN coding sequence. This divergence resulted in seventeen amino acid substitutions in the amino acid sequence of the protein encoded by the PIV-3 HN gene.

Figure 6:
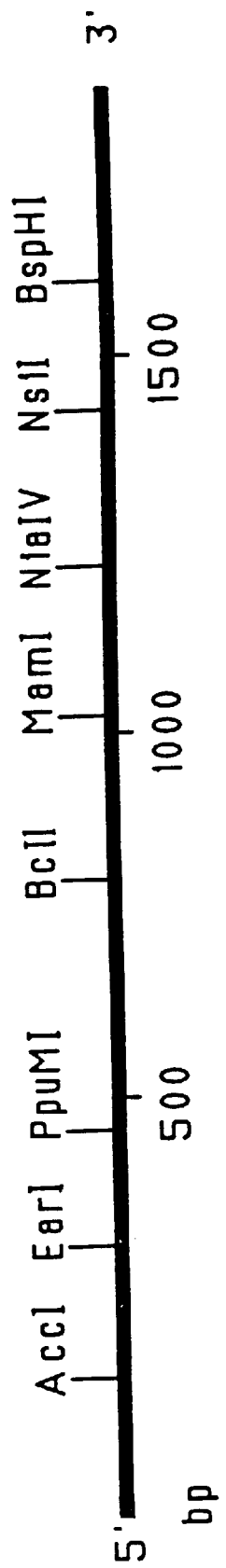
FIG. 6 shows the restriction map of the RSV F gene.

The nucleotide (SEQ ID No:5) and amino acid (SEQ ID No:6) sequences of the RSV F gene and RSV F protein, respectively, are shown in FIG. 5 and the restriction map of the gene is shown in FIG. 6. Analysis of the 1887 nucleotide sequence from two RSV F clones verified complete sequence homology between the two clones. Comparison of this nucleotide sequence with that reported for the RSV F gene revealed approximately 1.8% divergence in the coding sequence resulting in eleven amino acid substitutions.

The nucleotide (SEQ ID No:7) and amino acid (SEQ ID No:8) sequences of the RSV G gene and RSV G protein, respectively, are presented in FIG. 7 while the restriction map of the gene is outlined in FIG. 8. Comparison of the 920 nucleotide sequence of the G gene clone with the published G sequence (type A isolate) revealed a 4.2% divergence in the nucleotide sequence and a 6.7% divergence in the amino acid sequence of the gene product. This divergence resulted in twenty amino acid substitutions.

The full-length PIV-3 F (non-PCR amplified), PIV-3 HN, RSV F and RSV G genes were cloned into λgtll and subcloned into the multiple cloning site of a Bluescript M13-SK vector, either by blunt end ligation or using appropriate linkers. The PCR-amplified PIV-3 F gene was directly cloned into the Bluescript vector. The cloning vectors containing the PIV-3 F-PCR amplified, PIV-3 F non-PCR amplified, PIV-3 HN, RSV F and RSV G genes were named pPI3F, pPI3Fc, pPIVHN, PRSVF and PRSVG, respectively.

Example 2

This Example illustrates the construction of a Bluescript-based expression vector (pMCR20) containing the chimeric $F_{PIV-3}$-$F_{RSV}$ gene. This chimeric gene construct contains the 5' untranslated region of the PIV-3 F gene but lacks the hydrophobic anchor and cytoplasmic tail coding regions of both the PIV-3 and RSV F genes. The steps involved in the construction of this plasmid are summarized in FIG. 9.

To prepare the PIV-3 portion of the chimeric gene (FIG. 9, step 1), the full length PIV-3 gene lacking the transmembrane region and cytoplasmic tail coding regions was retrieved from plasmid pPI3F by cutting the polylinker with BamHI, blunt-ending the linearized plasmid with Klenow polymerase and cutting the gene with BsrI. A BsrI-BamHI oligonucleotide cassette (SEQ ID No:9) containing a PpuMI site and three successive translational stop codons were ligated to the truncated 1.6 Kb [BamHI]-BsrI PIV-3 F gene fragment and cloned into the EcoRV-BamHI sites of a Bluescript M13-SK expression vector containing the human methallothionen promoter and the polyA and IVS sequences of the SV40 genome (designated pMCR20), to generate plasmid pME1.

To engineer the RSV F gene component of the chimeric construct (FIG. 9, step 2), the RSV F gene lacking the transmembrane region and cytoplasmic tail coding regions was retrieved from plasmid pRSVF by cutting the polylinker with EcoRI and the gene with BspHI. A synthetic BspHI-BamHI oligonucleotide cassette (SEQ ID No:10) containing three successive translational stop codons was ligated to the 1.6 Kb truncated RSV F gene and cloned into the EcoRI-BamHI sites of the Bluescript based expression vector, pMCR20 to produce plasmid pES13A. Plasmid pES13A then was cut with EcoRI and PpuMI to remove the leader and F2 coding sequences from the truncated RSV F gene. The leader sequence was reconstructed using an EcoRI-PpuMI oligocassette (SEQ ID No:11) and ligated to the RSV F1 gene segment to generate plasmid pES23A.

To prepare the chimeric $F_{PIV-3}$-$F_{RSV}$ gene (FIG. 9, step 3) containing the 5' untranslated region of the PIV-3 F gene linked to the truncated RSV F1 gene fragment, plasmid pME1 (containing the 1.6 Kb truncated PIV-3 F gene) first was cut with PpuMI and BamHI. The PpuMI-BamHI restricted pME1 vector was dephosphorylated with intestinal alkaline phosphatase. The 1.1 Kb RSV F1 gene fragment was retrieved from plasmid pES23A by cutting the plasmid with PpuMI and BamHI. The 1.1 Kb PpuMI-BamHI RSV F1 gene fragment was cloned into the PpuMI-BamHI sites of the dephosphorylated pME1 vector to generate plasmid pES29A. This chimeric gene construct contains the 5' untranslated region of the PIV-3 F gene but lacks the nucleotide sequences coding for the hydrophobic anchor domains and cytoplasmic tails of both the PIV-3 and RSV F proteins.

Example 3

This Example illustrates the construction of a Bluescript-based expression vector containing the PIV-3 F gene lacking both the 5' untranslated and transmembrane anchor and cytoplasmic tail coding regions. The steps involved in constructing this plasmid are outlined in FIG. 10.

Plasmid pPI3F containing the full length PIV-3 F gene was cut with BamHI, blunt ended with Klenow polymerase and then cut with BsrI to remove the transmembrane and cytoplasmic tail coding regions. The Bluescript-based expression vector, pMCR20, was cut with SmaI and BamHI. A synthetic BsrI-BamHI oligonucleotide cassette (SEQ ID No:12) containing a translational stop codon was ligated with the 1.6 Kb blunt ended-BsrI PIV-3 F gene fragment to the SmaI-BamHI restricted pMCR20 vector to produce plasmid pMpFB. The PIV-3 F gene of this construct lacked the DNA fragment coding for the transmembrane and cytoplasmic anchor domains but contained the 5' untranslated region. To engineer a plasmid containing the PIV-3 F gene devoid of both the 5' untranslated region and the DNA fragment coding for the hydrophobic anchor domain, plasmid pMpFB was cut with EcoRI and BstBI. An EcoRI-BstBI oligocassette (SEQ ID No:13) containing the sequences to reconstruct the signal peptide and coding sequences removed by the EcoRI-BstBI cut was ligated to the EcoRI-BstBI restricted pMpFB vector to produce plasmid pMpFA.

Example 4

This Example illustrates the construction of the chimeric $F_{PIV-3}$-$F_{RSV}$ gene composed of the truncated PIV-3 F gene devoid of the 5' untranslated region linked to the truncated RSV F1 gene. The steps involved in constructing this plasmid are summarized in FIG. 11.

To prepare this chimeric gene construct, plasmid pES29A (Example 2) was cut with BstBI and BamHI to release the 2.5 Kb BstBI-BamHI PI3-3 F-RSV F1 chimeric gene fragment. This BstBI-BamHI fragment was isolated from a low melting point agarose gel and cloned into the BstBI-BamHI sites of the dephosphorylated vector pMpFA to produce plasmid pES60A. This construct contained the PIV-3 F gene lacking both the 5' untranslated region and the hydrophobic anchor and cytoplasmic tail coding sequences linked to the F1 coding region of the truncated RSV F gene. This chimeric gene was subsequently subcloned into the baculovirus transfer vector (see Example 5).

Example 5

Figure 12B:
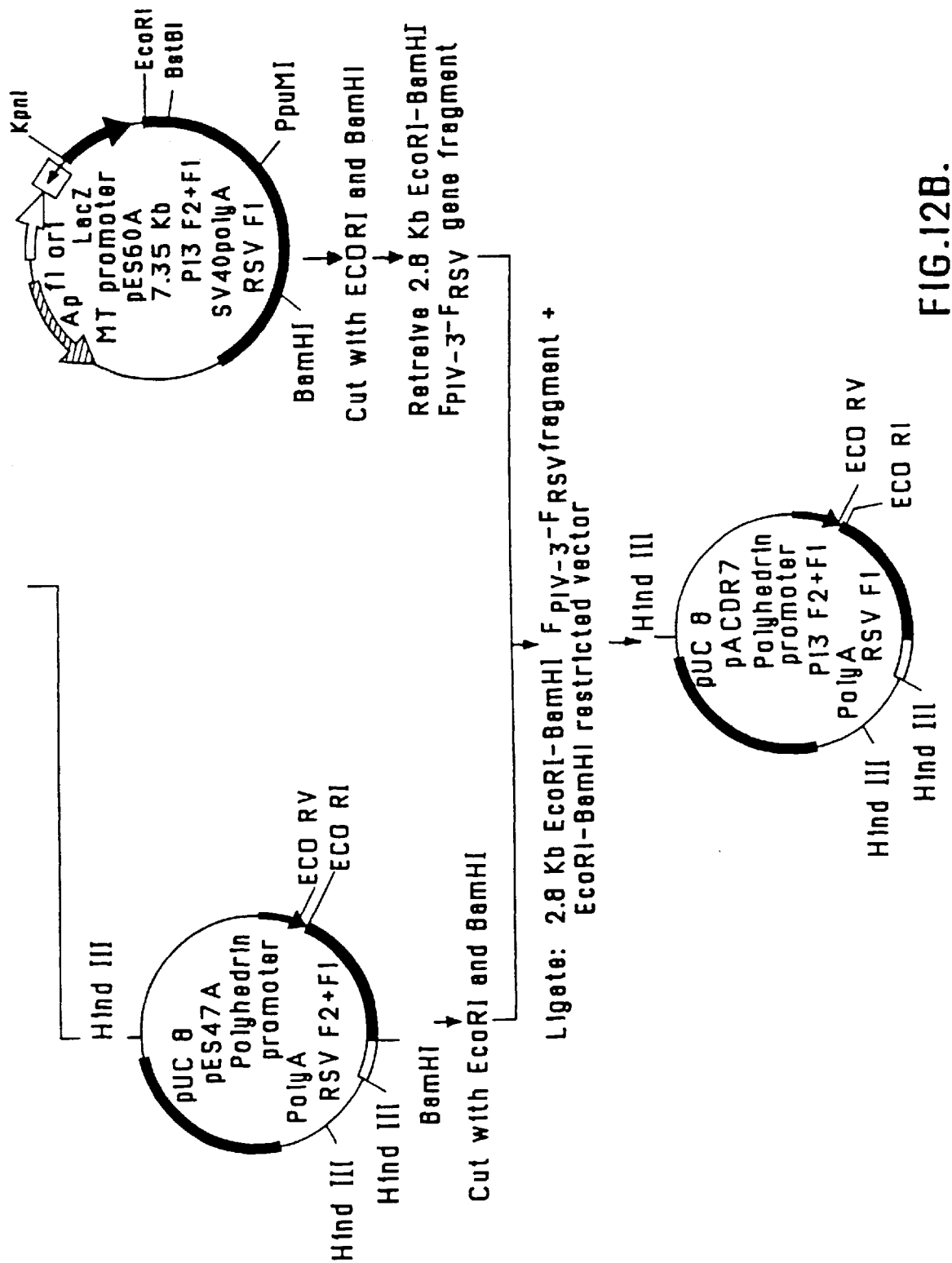
FIG. 12 shows the steps involved in construction of a modified pAC 610 baculovirus expression vector containing a chimeric $F_{PIV-3}$-$F_{RSV}$ gene consisting of the PIV-3 F gene lacking both the 5'-untranslated sequence as well as transmembrane and cytoplasmic tail coding region linked to the truncated RSV F1 gene.

This Example illustrates the construction of the modified pAC 610 baculovirus transfer vector containing the native polyhedrin promoter and the chimeric $F_{PIV-3}$-$F_{RSV}$ gene consisting of the PIV-3 F gene lacking both the 5' untranslated sequence and the nucleotide sequence coding for the hydrophobic anchor domain and cytoplasmic tail linked to the truncated RSV F1 gene. Construction of this plasmid is illustrated in FIG. 12.

The pAC 610 baculovirus expression vector was modified to contain the native polyhedrin promoter in the following manner. Vector pAC 610 was cut with EcoRV and BamHI. The 9.4 Kb baculovirus transfer vector lacking the EcoRV-BamHI DNA sequence was isolated from a low melting point agarose gel and treated with intestinal alkaline phosphatase. In a 3-way ligation, an EcoRV-EcoRI oligonucleotide cassette (SEQ ID No:14) containing the nucleotides required to restore the native polyhedrin promoter was ligated with the 1.6 Kb EcoRI-BamHI truncated RSV F gene fragment isolated from construct pES13A (Example 2, step 2) and the EcoRV-BamHI restricted pAC 610 phosphatased vector to generate plasmid pES47A. To prepare the pAC 610 based expression vector containing the chimeric $F_{PIV-3}$-$F_{RSV}$ gene, plasmid pES47A was first cut with EcoRI and BamHI to remove the 1.6 Kb truncated RSV F gene insert. The 2.8 Kb $F_{PIV-3}$-$F_{RSV}$ chimeric gene was retrieved by cutting plasmid pES60A (Example 4) with EcoRI and BamHI. The 2.8 Kb EcoRI-BamHI chimeric gene was ligated to the EcoRI-BamHI restricted pES47A vector to generate plasmid pAC DR7 (ATCC 75387).

Example 6

This Example outlines the preparation of plaque-purified recombinant baculoviruses containing the chimeric $F_{PIV-3}$-$F_{RSV}$ gene.

*Spodoptera frugiperda* (Sf9) cells were co-transfected with 1.0 μg wild-type AcMNPV DNA and 2.5 μg of $F_{PIV-3}$-$F_{RSV}$ plasmid DNA (plasmid pAC DR7—Example 5). Putative recombinant baculoviruses (purified once by serial dilution) containing the $F_{PIV-3}$-$F_{RSV}$ chimeric gene were identified by dot-blot hybridization. Lysates of insect cells infected with the putative recombinant baculoviruses were probed with the $^{32}$P-labelled $F_{PIV-3}$-$F_{RSV}$ chimeric gene insert. Recombinant baculoviruses were plaque-purified twice before being used for expression studies. All procedures were carried out according to the protocols outlined by M.D. Summers and G. E. Smith in "A Manual of Methods for Baculovirus Vectors and Insect Cell Culture Procedures", Texas Agricultural Experiment Station, Bulletin 1555, 1987.

Example 7

This Example illustrates the presence of the chimeric $F_{PIV-3}$-$F_{RSV}$ protein in supernatants and cell lysates of infected Sf9 cells.

Insect cells were infected with the plaque-purified recombinant baculoviruses prepared as described in Example 6 at a m.o.i. of 8. Concentrated supernatants from cells infected with the recombinant viruses were positive in a PIV-3 F specific ELISA. In addition, when lysates from $^{35}$S-methioninelabelled infected cells were subjected to SDS-polyacrylamide gel electrophoresis and gels were analyzed by autoradiography, a strong band with apparent molecular weight of approximately 90 kDa was present in lysates of cells infected with the recombinant viruses but was absent in the lysates from wild-type infected cells. The presence of the chimeric $F_{PIV-3}$-$F_{RSV}$ protein in the lysates of cells infected with the recombinant baculoviruses was confirmed further by Western blot analysis using monospecific anti-PIV-3 F and anti-RSV F antisera and/or monoclonal antibodies (Mabs). Lysates from cells infected with the recombinant baculoviruses reacted with both anti-PIV-3 and anti-RSV antisera in immunoblots. As shown in the immunoblot of FIG. 13, lysates from cells infected with either the RSV F or $F_{PIV-3}$-$F_{RSV}$ recombinant baculoviruses reacted positively with the anti-F RSV Mab. As expected, lysates from cells infected with wild type virus did not react with this Mab. In addition, only lysates from cells infected with the chimeric $F_{PIV-3}$-$F_{RSV}$ recombinant viruses reacted with the anti-PIV-3 $F_1$ antiserum.

Example 8

This Example illustrates modification of the baculovirus transfer vector pVL1392 (obtained from Invitrogen), wherein the polyhedrin ATG start codon was converted to ATT and the sequence CCG was present downstream of the polyhedrin gene at positions +4,5,6. Insertion of a structural gene several base pairs downstream from the ATT codon is known to enhance translation. The steps involved in constructing this modified baculovirus transfer vector are outlined in FIG. 14.

The baculovirus expression vector pVL1392 was cut with EcoRV and BamHI. The 9.5 kb restricted pVL1392 vector was ligated to an EcoRV-BamHI oligonucleotide cassette (SEQ ID No:15) to produce the pD2 vector.

Example 9

This Example illustrates the construction of the pD2 baculovirus expression vector containing the chimeric $F_{RSV}$-$HN_{PIV-3}$ gene consisting of the truncated RSV F and PIV-3 HN genes linked in tandem. The steps involved in constructing this plasmid are summarized in FIG. 15.

To engineer the $F_{RSV}$-$HN_{PIV-3}$ gene, the RSV F gene lacking the nucleotide sequence coding for the transmembrane domain and cytoplasmic tail of the RSV F glycoprotein was retrieved from plasmid PRSVF (Example 1) by cutting the polylinker with EcoRI and the gene with BspHI. The PIV-3 HN gene devoid of the DNA fragment coding for the hydrophobic anchor domain was retrieved from plasmid pPIVHN (Example 1) by cutting the gene with BspHI and the polylinker with BamHI. The 1.6 Kb EcoRI-BspHI RSV F gene fragment and the 1.7 Kb BspHI-BamHI PIV-3 HN gene fragment were isolated from low melting point agarose gels. For cloning purposes, the two BspHI sites in the Bluescript based mammalian cell expression vector, pMCR20, were mutated. Mutations were introduced in the BspHI sites of the pMCR20 by cutting the expression vector with BspHI, treating both the BspHI restricted vector and the 1.1 Kb fragment released by the BspHI cut with Klenow polymerase and ligating the blunt-ended 1.1 Kb fragment to the blunt-ended Bluescript-based expression vector to generate plasmid pM'. Since insertion of the 1.1 Kb blunt-end fragment in the mammalian cell expression vector in the improper orientation would alter the Amp$^r$ gene of the Bluescript-based expression vector, only colonies of HB101 cells transformed with the pM' plasmid DNA with the 1.1 Kb blunt-ended fragment in the proper orientation could survive in the presence of ampicillin. Plasmid DNA was purified from ampicillin-resistant colonies of HB101 cells transformed with plasmid pM' by equilibrium centrifugation in cesium chloride-ethidium bromide gradients. The 1.6 Kb EcoRI-BspHI RSV F and 1.7 Kb BspHI-BamHI PIV-3 HN gene fragments were directly cloned into the EcoRI-BamHI sites of vector pM' in a 3-way ligation to generate plasmid pM' RF-HN.

To restore specific coding sequences of the RSV F and PIV-3 HN genes removed by the BspHI cut, a BspHI-BspHI oligonucleotide cassette (SEQ ID No:16) containing the pertinent RSV F and PIV-3 HN gene sequences was ligated via the BspHI site to the BspHI-restricted plasmid pM' RF-HN to produce plasmid pM RF-HN. Clones containing the BspHI-BspHI oligonucleotide cassette in the proper orientation were identified by sequence analysis of the oligonucleotide linker and its flanking regions.

To clone the chimeric $F_{RSV}$-$HN_{PIV-3}$ gene into the baculovirus expression vector pD2 (Example 8), the $F_{RSV}$-$HN_{PIV-3}$ truncated gene first was retrieved from plasmid pM RF-HN by cutting the plasmid with EcoRI. The 3.3 Kb $F_{RSV}$-$HN_{PIV-3}$ gene then was cloned into the EcoRI site of the baculovirus transfer vector plasmid pD2 to generate plasmid pD2 RF-HN (ATCC 75388). Proper orientation of the 3.3 Kb EcoRI $F_{RSV}$-$HN_{PIV-3}$ chimeric gene insert in plasmid pD2 RF-HN was confirmed by sequence analysis.

Example 10

This Example outlines the preparation of plaque-purified recombinant baculoviruses containing the chimeric $F_{RSV}$-$HN_{PIV-3}$ gene.

*Spodoptera frugiperda* (Sf9) cells were co-transfected with 1 μg wild-type AcNPV DNA and 2 μg of $F_{RSV}$-$HN_{PIV-3}$ plasmid DNA (plasmid pD2 RF-HN-Example 9). Putative recombinant baculoviruses (purified once by serial dilution) containing the $F_{RSV}$-$HN_{PIV-3}$ chimeric gene were identified by dot-blot hybridization. Lysates of insect cells infected with the putative recombinant baculoviruses were probed with the $^{32}$P-labelled RSV F or PTV-3 HN gene oligonucleotide probes. Recombinant baculoviruses were plaque-purified three times before being used for expression studies. All procedures were carried out according to the protocols outlined by Summers and Smith (Example 6).

Example 11

This Example illustrates the presence of the chimeric $F_{RSV}$-$HN_{PIV-3}$ protein in supernatants of infected Sf9 and High 5 cells.

Insect cells (Sf9 and High 5), maintained in serum free medium EX401, were infected with the plaque purified recombinant baculoviruses of Example 10 at a m.o.i. of 5 to 10 pfu/cell. Supernatants from cells infected with the recombinant baculoviruses tested positive for expressed protein in both the RSV-F and PIV-3 HN specific ELISAS. In addition, supernatants from infected cells reacted positively with both an anti-F RSV monoclonal antibody and anti-HN peptide antisera on immunoblots. A distinct band of approximately 105 kDa was present in the immunoblots. These results confirm the secretion of the chimeric $F_{RSV}$-$HN_{PIV-3}$ protein into the supernatant of Sf9 and High 5 cells infected with the recombinant baculoviruses.

Example 12

This Example illustrates the purification of the chimeric $F_{RSV}$-$HN_{PIV-3}$ protein from the supernatants of infected High 5 cells.

High 5 cells, maintained in serum free medium, were infected with the plaque purified recombinant baculoviruses of Example 10 at a m.o.i of 5 pfu/cell. The supernatant from virus infected cells was harvested 2 days post-infection. The soluble $F_{RSV}$-$HN_{PIV-3}$ chimeric protein was purified from the supernatants of infected cells by immunoaffinity chromatography using an anti-HN PIV-3 monoclonal antibody. The anti-HN monoclonal antibody was coupled to CNBr-activated Sepharose 4B by conventional techniques. The immunoaffinity column was washed with 10 bed volumes of washing buffer (10 mM Tris-HCl pH 7.5, 150 mM NaCl, 0.02% v/v TRITON-X 100) (Trademark for a non-ionic detergent) prior to use. After sample loading, the column was washed with 10 bed volumes of washing buffer followed by 3 bed volumes of high salt buffer (10 mm Tris-HCl pH 7.5, 500 mM NaCl, 0.02% v/v Triton-X 100) . The chimeric $F_{RSV}$-$HN_{PIV-3}$ protein was eluted from the immunoaffinity column with 100 MM glycine, pH 2.5, in the presence of 0.02% TRITON X-100. Eluted protein was neutralized immediately with 1M Tris-HCl, pH 10.7.

Polyacrylamide gel electrophoretic analysis (FIG. 16, panel A) of the immunoaffinity-purified $F_{RSV}$-$HN_{PIV-3}$ protein revealed the presence of one major protein band with an apparent molecular weight of 105 kDa. The purified protein reacted with both an anti-RSV F monoclonal antibody and anti-HN peptide antisera on immunoblots (FIG. 16, panel B, lanes 1 and 2, respectively).

Example 13

This Example illustrates the immunogenicity of the $F_{RSV}$-$HN_{PIV-3}$ protein in guinea pigs.

Groups of four guinea pigs were injected intramuscularly with either 1.0 or 10.0 μg of the chimeric $F_{RSV}$-$HN_{PIV-3}$ protein purified as described in Example 12 and adjuvanted with aluminum phosphate. Groups of control animals were immunized with either placebo, or live PIV-3 or RSV (administered intranasally). Guinea pigs were bled 2 and 4 weeks after the primary injection and boosted at 4 weeks with an equivalent dose of the antigen formulation. Serum samples also were taken 2 and 4 weeks after the booster dose. To assess the ability of the chimeric protein to elicit PIV-3 and RSV-specific antibody responses, sera samples were analyzed for the presence of PIV-3 specific hemagglutination inhibiting and neutralizing antibodies as well as RSV neutralizing antibodies. As summarized in Table 1 below (the Tables appear at the end of the disclosure), the sera of animals immunized with two 10 μg doses of the chimeric protein had titres of PIV-3 specific hemagglutination inhibition (HAI) and PIV-3/RSV neutralizing antibodies at the 6 and 8 week time points which were equivalent to the levels obtained following intranasal inoculation with either live PIV-3 or RSV. In addition, animals immunized with only two 1 ug doses of the chimeric protein elicited strong PIV-3 and RSV specific neutralizing antibodies. These results confirmed the immunogenicity of both the RSV and PIV-3 components of the chimeric protein and provided confirmatory evidence that a single recombinant immunogen can elicit neutralizing antibodies against both RSV and PIV-3.

Example 14

This Example illustrates the immunogenicity and protective ability of the $F_{RSV}$-$HN_{PIV-3}$ protein in cotton rats.

Groups of eight cotton rats were injected intramuscularly with either 1.0 or 10.0 ug of the chimeric $F_{RSV}$-$HN_{PIV-3}$ protein (prepared as described in Example 12) adjuvanted with aluminum phosphate. Groups of control animals were immunized with either placebo (PBS+aluminum phosphate) or live PIV-3 or RSV (administered intranasally). Cotton rats were bled 4 weeks after the primary injection and boosted at 4 weeks with an equivalent dose of the antigen formulation. Serum samples were also taken 1 week after the booster dose. As shown in Table 2 below, data from the 4-week bleed demonstrated that both a 1 and 10 μg dose of the chimeric protein was capable of inducing a strong primary response. Reciprocal mean $log_2$ PIV-3 specific HAI and PIV-3/RSV neutralizing titers were equivalent to the titres obtained with live PIV-3 and RSV. Thus, a single inoculation of the chimeric protein was sufficient to elicit neutralizing antibodies against both PIV-3 and RSV. Strong neutralizing PIV-3 and RSV titres also were observed following the booster dose (5 week bleed). These results provide additional evidence that both the RSV and PIV-3 components of the chimeric protein are highly immunogenic.

To assess the ability of the chimeric immunogen to simultaneously protect animals against both RSV and PIV-3, four cotton rats from each group were challenged intranasally with 100 $TCID_{50}$ units of either PIV-3 or RSV. Animals were killed 4 days after virus challenge. Virus titers were determined in lung lavages. As shown in Table 3 below, animals immunized with either 1 or 10 μg of the chimeric $F_{RSV}$-$HN_{PIV-3}$ protein were completely protected against challenge with either PIV-3 or RSV. These results provide evidence that the chimeric protein is not only highly immunogenic but can also simultaneously protect cotton rats against disease caused by both PIV-3 and RSV infection.

Example 15

Figure 18:
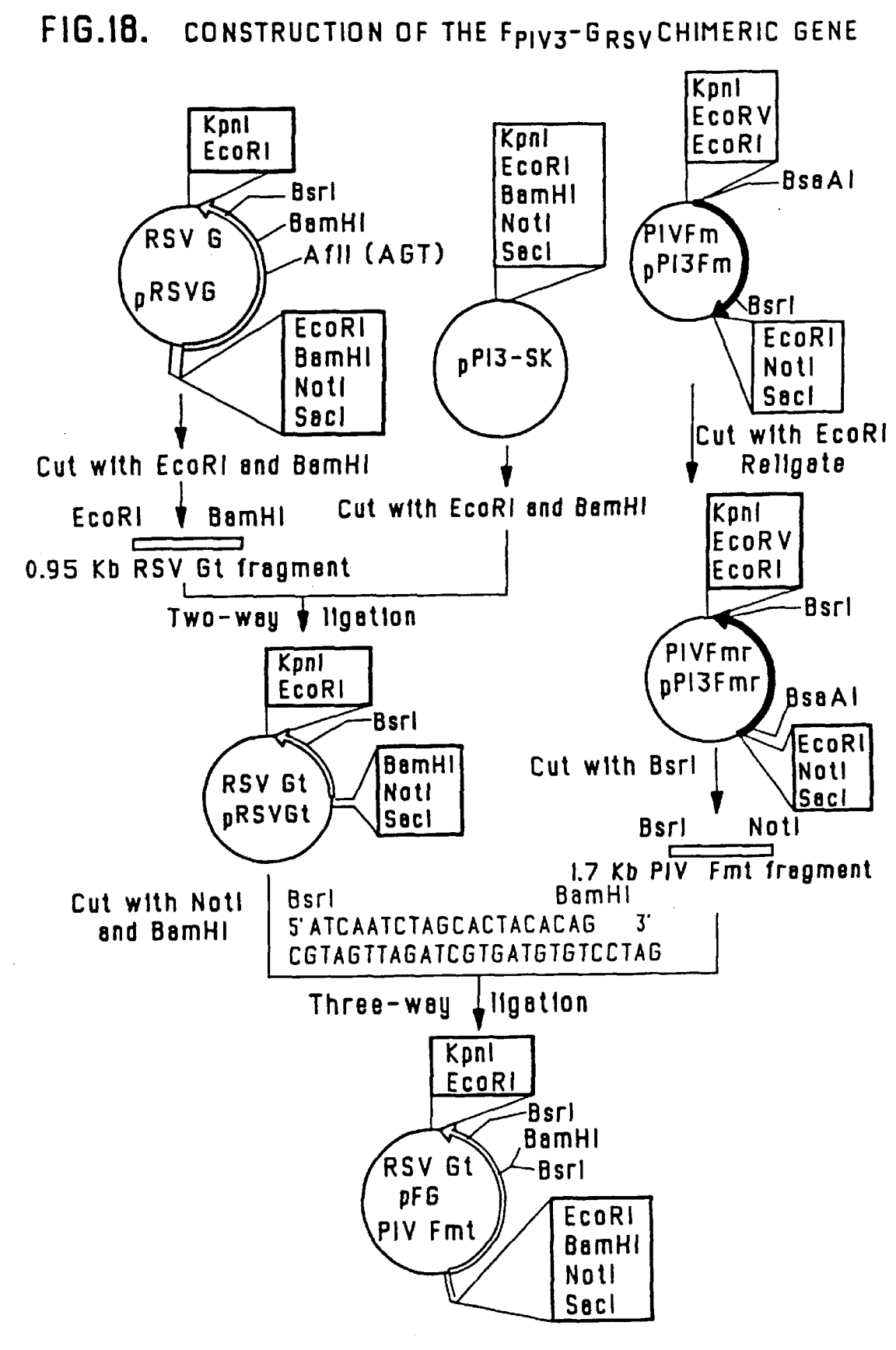

This Example illustrates the construction of a Bluescript M13-SK vector containing the chimeric $F_{PIV-3}$-$G_{RSV}$ gene. This chimeric gene construct contains the 5' untranslated region of a mutated PIV-3 F gene but lacks the nucleotide sequence coding for the hydrophobic anchor and cytoplasmic tail domains of both a mutated PIV-3 F and the native RSV G genes. The steps involved in constructing this plasmid are outlined in FIGS. 17 and 18.

The first step (FIG. 17) involved in preparing the PIV-3 F component of the chimeric $F_{PIV-3}$-$G_{RSV}$ gene construct was to eliminate the putative pre-termination sites within the 18 nucleotide long sequence 5' CAAGAAAAAGGAATAAAA 3' (SEQ ID No:17) located between positions 857 and 874 of the non PCR-amplified PIV-3 F gene and positions 847 and 864 of the PCR-amplified PIV-3 F gene (see FIG. 1). To this end, the PIV-F cDNA of the non-PCR amplified PIV-3

F gene was cut at the BsaAI and EcoRI sites. The BsaAI-EcoRI PIV F gene fragment was cloned into the EcoRI site of a Bluescript M13-SK vector using an EcoRI-BsaAI linker. The 857–874 target region of the PIV-3 F gene (non-PCR amplified) then was mutated by oligonucleotide-mediated mutagenesis using the method of Morinaga et al. [1984, Biotechnology 2:636–639]. Plasmid pPI3Fc (Example 1) was cut with ScaI in the Amp$^r$ gene and dephosphorylated with alkaline phosphatase (plasmid #1). A second sample of plasmid pPI3Fc was cut with BstEII and NsiI to produce a 3.9 Kb restricted plasmid, lacking the 0.9 Kb BstEII-NsiI fragment of the PIV-3 F gene (plasmid #2). A mutagenic 78-mer synthetic oligonucleotide (#2721 shown in FIG. 17-SEQ ID No:18)) containing the sequence 5' CAGGAGAAGGGTATCAAG 3' (SEQ ID No:19) was synthesized to specifically mutate the 857–874 DNA segment without changing the F protein sequence. This oligonucleotide was added to plasmid DNAs #1 and #2, denatured at 100° C. for 3 min. and renatured by gradual cooling. The mixture then was incubated in the presence of DNA polymerase, dNTPs and T4 ligase and transformed into HB101 cells. Bacteria containing the 1.8 Kb mutated PIV-3 F gene were isolated on YT agar plates containing 100 μg/ml ampicillin. Hybridization with the oligonucleotide probe 5' AGGAGAAGGGTATCAAG 3' (SEQ ID No: 20) was used to confirm the presence of the mutated PIV-3 F gene. The mutated gene sequence was confirmed by DNA sequencing. The plasmid containing the mutated PIV-3 gene was designated pPI3Fm.

The second step (FIG. 18) in the engineering of the chimeric gene construct involved constructing a Bluescript based vector to contain the truncated PIV-3 Fm gene lacking the nucleotide sequence coding for the transmembrane anchor domain and cytoplasmic tail of the PIV-3 F protein linked in tandem with the RSV G gene lacking both the 5' leader sequence and the nucleotide sequence coding for the transmembrane anchor domain and cytoplasmic tail of the G glycoprotein.

To prepare this chimeric gene, the orientation of the mutated PIV-F gene in plasmid pPI3Fm first was reversed by EcoRI digestion and religation to generate plasmid pPI3Fmr. To prepare the PIV-3 F gene component of the chimeric gene, plasmid pPI3Fmr was cut with NotI and BsrI to release the 1.7 Kb truncated PIV-3 F gene. To prepare the RSV G component, the 0.95 Kb RSV-G gene lacking both the 5' leader sequence and the DNA segment encoding the G protein anchor domain and cytoplasmic tail was released from plasmid pRSVG (Example 1) by cutting the polylinker with EcoRI and the gene with BamHI. The 0.95 Kb EcoRI-BamHI RSV G gene fragment was subcloned into the EcoRI-BamHI sites of a restricted Bluescript vector, pM13-SK, to produce plasmid pRSVGt. The 0.95 Kb EcoRI-BamHI G gene fragment and the 1.5 Kb NotI-BsrI truncated PIV-3 F gene were linked via a BsrI-BamHI oligonucleotide cassette (SEQ ID No:9) restoring the F and G gene coding sequences and cloned into the pRSVGt vector restricted with BamHI and NotI in a 3-way ligation. The plasmid thus generated was designated pFG.

Example 16

This Example outlines the construction of the pD2 baculovirus transfer vector (described in Example 8) containing the chimeric $F_{PIV-3}$-$G_{RSV}$ gene consisting of a mutated PIV-3 F gene lacking the hydrophobic anchor and cytoplasmic coding regions linked to the RSV G gene lacking both the 5' leader sequence and the nucleotide sequences encoding the transmembrane anchor domain and cytoplasmic tail of the G protein.

To prepare this construct, plasmid pFG (Example 15) was cut with EcoRI to release the 2.6 Kb $F_{PIV-3}$-$G_{RSV}$ chimeric gene. The 2.6 Kb EcoRI restricted chimeric gene fragment then was sub-cloned into the EcoRI site of the dephosphorylated pD2 vector to generate the 12.1 Kb plasmid pD2F-G (ATCC 75389).

Example 17

This Example outlines the preparation of plaque-purified recombinant baculoviruses containing the chimeric $F_{PIV-3}$-$G_{RSV}$ gene.

*Spodoptera frugiperda* (Sf9) cells were co-transfected with 2 ug of pD2F-G plasmid DNA (Example 16) and 1 ug of linear wild-type AcNPV DNA (obtained from Invitrogen). Recombinant baculoviruses containing the $F_{PIV-3}$-$G_{RSV}$ gene were plaque-purified twice according to the procedure outlined in Example 10.

Example 18

This Example illustrates the presence of the chimeric $F_{PIV-3}$-$G_{RSV}$ protein in the supernatant of Sf9 and High 5 cells infected with the recombinant baculoviruses.

Sf9 and High 5 cells were infected with recombinant baculoviruses containing the $F_{PIV-3}$-$G_{RSV}$ gene (Example 16) at a m.o.i. of 5 to 10 pfu/cell. The supernatant of cells infected with the recombinant viruses tested positive for expressed protein in the PIV-3 F specific ELISA. Supernatants of infected cells reacted with both anti-F PIV-3 and anti-G RSV monoclonal antibodies in immunoblots. These results confirm the presence of the chimeric $F_{PIV-3}$-$G_{RSV}$ protein in the supernatants of infected Sf9 and High 5 cells.

Example 19

This Example outlines the preparation of recombinant vaccinia viruses expressing the $F_{PIV-3}$-$F_{RSV}$ and $F_{RSV}$-$HN_{PIV-3}$ genes.

Vaccinia virus recombinant viruses expressing the $F_{PIV-3}$-$F_{RSV}$ (designated vP1192) and $F_{RSV}$-$HN_{PIV-3}$ (designated vP1195) genes were produced at Virogenetics Corporation (Troy, N.Y.) (an entity related to assignee hereof) using the COPAK host-range selection system. Insertion plasmids used in the COPAK host-range selection system contained the vaccinia K1L host-range gene [Perkus et al., (1990) Virology 179:276–286] and the modified vaccinia H6 promoter [Perkus et al. (1989), J. Virology 63:3829–3836]. In these insertion plasmids, the K1L gene, H6 promoter and polylinker region are situated between Copenhagen strain vaccinia flanking arms replacing the ATI region [open reading frames (ORFs) A25L, A26L; Goebel et al., (1990), Virology 179:247–266; 517–563]. COPAK insertion plasmids are designed for use in in vivo recombination using the rescue virus NYVAC (vP866) (Tartaglia et al., (1992) Virology 188:217–232). Selection of recombinant viruses was done on rabbit kidney cells.

Recombinant viruses, vP1192 and vP1195 were generated using insertion plasmids pES229A-6 and PSD.RN, respectively. To prepare plasmid pES229A-6 containing the $F_{PIV-3}$-$F_{RSV}$ gene, the COPAK-H6 insertion plasmid pSD555 was cut with SmaI and dephosphorylated with intestinal alkaline phosphatase. The 2.6 Kb $F_{PIV-3}$-$F_{RSV}$ gene was retrieved from plasmid pES60A (Example 4) by cutting the plasmid with EcoRI and BamHI. The 2.6 Kb EcoRI-BamHI $F_{PIV-3}$-$F_{RSV}$ gene was blunt ended with Klenow polymerase, isolated from a low melting point agarose gel and cloned into the SmaI site of the COPAK-H6 insertion plasmid pSD555 to generate plasmid pES229A-6. This positioned the $F_{PIV-3}$-$F_{RSV}$ ORF such that the 5' end is nearest the H6 promoter.

To prepare plasmid PSD.RN, the pSD555 vector first was cut with SmaI and BamHI. Plasmid pM RF-HN (Example 9) containing the truncated $F_{RSV}$-$HN_{PIV-3}$ gene was cut with ClaI, blunt ended with Klenow polymerase and then cut with BamHI. The 3.3 Kb $F_{RSV}$-$HN_{PIV-3}$ gene was cloned into the SmaI-BamHI sites of the pSD555 vector to generate plasmid PSD.RN. This positioned the $F_{RSV}$-$HN_{PIV-3}$ ORF such that the H6 5' end is nearest the H6 promoter.

Plasmids pES229A-6 and PSD.RN were used in in vitro recombination experiments in vero cells with NYVAC (vP866) as the rescuing virus. Recombinant progeny virus was selected on rabbit kidney (RK)-13 cells (ATCC #CCL37). Several plaques were passaged two times on RK-13 cells. Virus containing the chimeric genes were confirmed by standard in situ plaque hybridization [Piccini et al. (1987), Methods in Enzymology, 153:545–563] using radiolabeled probes specific for the PIV and RSV inserted DNA sequences. Plaque purified virus containing the $F_{PIV-3}$-$F_{RSV}$ and $F_{RSV}$-$HN_{PIV-3}$ chimeric genes were designated vP1192 and vP1195, respectively.

Radioimmunoprecipitation was done to confirm the expression of the chimeric genes in vP1192 and vP1195 infected cells. These assays were performed with lysates prepared from infected Vero cells [according to the procedure of Taylor et al., (1990) J. Virology 64, 1441–1450] using guinea pig monospecific PIV-3 anti-HN and anti-F antiserum and rabbit anti-RSV F antiserum. Both the anti-PIV F and anti-RSV F antisera precipitated a protein with an apparent molecular weight of approximately 90 koa from vP1192 infected Vero cells. Both anti-RSV F and guinea pig anti-PIV HN antisera precipitated a protein with an apparent molecular weight of approximately 100 kDa from vP1195 infected cells. These results confirmed the production of the $F_{PIV-3}$-$F_{RSV}$ and $F_{RSV}$-$HN_{PIV-3}$ chimeric proteins in Vero cells infected with the recombinant poxviruses.

SUMMARY OF DISCLOSURE

In summary of the disclosure, the present invention provides multimeric hybrid genes which produce chimeric proteins capable of eliciting protection against infection by a plurality of pathogens, particularly PIV and RSV. Modifications are possible within the scope of this invention.

TABLE 1

Secondary antibody response of guinea pigs immunized with the chimeric $F_{RSV}$ - $HN_{PIV-3}$ protein

| | | HAI Titre[a] ($\log_2$ ± s.e.) | | Neutralization Titre[b] ($\log_2$ ± s.e.) | | |
|---|---|---|---|---|---|---|
| Antigen | Dose | PIV-3 | | PIV-3 | | RSV |
| Formulation | (μg) | 6 wk Bleed | 8 wk Bleed | 6 wk Bleed | 8 wk Bleed | 6 wk Bleed | 8 wk Bleed |
| Buffer | — | <1.0 ± 0.0 | <1.0 ± 0.0 | <1.0 ± 0.0 | <1.0 ± 0.0 | <1.0 ± 0.0 | <1.0 ± 0.0 |
| $F_{RSV}$ - $HN_{PIV-3}$ | 10.0 | 9.1 ± 0.3 | 9.1 ± 0.3 | 7.1 ± 0.3 | 7.1 ± 0.5 | 5.5 ± 0.9 | 4.5 ± 1.2 |
| | 1.0 | 7.0 ± 2.0 | 7.3 ± 2.2 | 5.0 ± 1.5 | 4.5 ± 1.4 | 4.5 ± 0.5 | 3.0 ± 1.0 |
| Live PIV-3 | | 8.6 ± 0.7 | 7.3 ± 0.6 | 7.0 ± 0.4 | 7.3 ± 0.6 | N/A | N/A |
| Live RSV | | N/A[c] | N/A | N/A | N/A | 5.5 ± 1.5 | 5.0 ± 1.0 |

[a]Reciprocal mean $\log_2$ serum dilution which inhibits erythrocyte agglutination by 4 hemagglutinating units of PIV-3
[b]Reciprocal mean $\log_2$ serum dilution which blocks hemadsorption of 100 $TCID_{50}$ units of PIV-3 or RSV
[c]N/A — not applicable

TABLE 2

Serum antibody response of cotton rats immunized with the chimeric $F_{RSV}$ - $HN_{PIV-3}$ protein[a]

| | | HAI Titre[b] ($\log_2$ ± s.d.) | | Neutralization Titre[c] ($\log_2$ ± s.d.) | | |
|---|---|---|---|---|---|---|
| Antigen | Dose | PIV-3 | | PIV-3 | | RSV |
| Formulation | (μg) | 4 wk Bleed | 5 wk Bleed | 4 wk Bleed | 5 wk Bleed | 4 wk Bleed | 5 wk Bleed |
| Buffer | — | 2.8 ± 0.5 | <3.0 ± 0.0 | <1.0 ± 1.0 | <1.0 ± 0.0 | 1.8 ± 0.3 | 0.8 ± 0.7 |
| $F_{RSV}$ - $HN_{PIV-3}$ | 10.0 | 9.5 ± 1.3 | 10.5 ± 0.6 | >9.0 ± 0.0 | >9.0 ± 0.0 | 5.2 ± 1.1 | 5.8 ± 0.9 |
| | 1.0 | 9.3 ± 1.0 | 10.3 ± 0.5 | >9.0 ± 0.0 | >9.0 ± 0.0 | 5.0 ± 0.7 | 5.8 ± 1.2 |
| Live PIV-3 | | 7.0 ± 0.0 | 8.5 ± 0.7 | >9.0 ± 0.0 | 9.2 ± 0.7 | N/A | N/A |
| Live RSA | | N/A[d] | N/A | N/A | N/A | 5.5 ± 0.6 | 8.5 ± 0.6 |

[a]Each value represents the mean titre af antisera from 8 animals.
[b]Reciprocal mean $\log_2$ serum diution which inhibits erythrocyte agglutination by 4 hemagglutinating units of PIV-3
[c]Reciprocal mean $\log_2$ serum dilution which blocks hemadsorption of 100 $TCID_{30}$ units of PIV-3 or RSV
[d]N/A — not applicable

TABLE 3

Response of immunized cotton rats to PIV/RSV challenge[a]

| Antigen Formation | Dose ($\mu$g) | Mean virus lung titre $\log_{10}$/g lung ± s.d. | |
|---|---|---|---|
| | | RSV | PIV-3 |
| Buffer | — | 3.7 ± 0.3 | 3.4 ± 0.3 |
| $F_{RSV}$ - $HN_{PIV-3}$ | 10.0 | ≤1.5 ± 0.0 | ≤1.5 ± 0.0 |
| $F_{RSV}$ - $HN_{PIV-3}$ | 1.0 | ≤1.5 ± 0.0 | ≤1.5 ± 0.0 |
| Live RSV | | ≤1.5 ± 0.0 | ≤1.5 ± 0.0 |
| Live PIV-3 | | ≤1.5 ± 0.0 | ≤1.5 ± 0.0 |

[a]Animals were challenged intranasally with 100 $TCID_{50}$ units of PIV-3 or RSV and killed 4 days later. Each value represents the mean virus lung titre of 4 animals.

What we claim is:

1. A multimeric hybrid gene encoding a chimeric protein, said hybrid gene being selected from the group consisting of:

(a) a hybrid gene comprising a nucleotide sequence coding for a native PIV-3 F protein linked to a nucleotide sequence coding for a native RSV G protein;

(b) a hybrid gene comprising a nucleotide sequence coding for a native PIV-3 F protein linked to a nucleotide sequence coding for a native RSV F protein;

(c) a hybrid gene comprising a nucleotide sequence coding for a native PIV-3 HN protein linked to a nucleotide sequence coding for a native RSV G protein; and (d) a hybrid gene comprising a nucleotide sequence coding for a native PIV-3 HN protein linked to a nucleotide sequence coding for a native RSV F protein.

2. The hybrid gene of claim 1 which is selected from the group consisting of $F_{PIV-3}$-$F_{RSV}$, $F_{RSV}$-$HN_{PIV-3}$ and $F_{PIV-3}$-$G_{RSV}$ hybrid genes.

3. The hybrid gene of claim 2 contained in an expression vector.

4. The hybrid gene of claim 3 the form of a plasmid selected from the group consisting of pAC DR7, pD2 RF-HN and pD2 F-G.

5. The hybrid gene of claim 1 further comprising at least one gene encoding at least one immunogenic and/or immunostimulating molecule.

6. Eukaryotic cells containing the multimeric hybrid gene of claim 1 for expression of said chimeric protein encoded by said gene.

7. A process for preparation of a chimeric protein, which comprises:

isolating a first nucleotide sequence coding for a native PIV-3 F protein or a first nucleotide sequence coding for a native PIV-3 HN protein, isolating a second nucleotide sequence coding for a native RSV G protein or a second nucleotide sequence coding for a native RSV F protein, linking said first and second nucleotide sequences to form a multimeric hybrid gene, said multimeric hybrid gene being selected from the group consisting of:

(a) a hybrid gene comprising a nucleotide sequence coding for a native PIV-3F protein linked to a nucleotide sequence coding for a native RSV G protein;

(b) a hybrid gene comprising a nucleotide sequence coding for a native PIV-3 F protein linked to a nucleotide sequence coding for a native RSV F protein;

(c) a hybrid gene comprising a nucleotide sequence coding for a native PIV-3 HN protein linked to a nucleotide sequence coding for a native RSV G protein; and (d) a hybrid gene comprising a nucleotide sequence coding for a native PIV-3 HN protein linked to a nucleotide sequence coding for a native RSV F protein; and expressing the multimeric hybrid gene in a eukaryotic cellular expression system.

8. The process of claim 7 wherein said multimeric hybrid gene is selected from the group consisting of $F_{PIV-3}$-$F_{RSV}$, $F_{RSV}$-$HN_{PIV-3}$ and $F_{PIV-3}$-$G_{RSV}$ hybrid genes.

9. The process of claim 8 wherein said multimeric hybrid gene is contained in an expression vector comprising a plasmid selected from the group consisting of pAC DR7, pD2 RF-HN and pD2 F-G.

10. The process of claim 7 including separating a chimeric protein from a culture of said eukaryotic cellular expression system and purifying the separated chimeric protein.

11. The hybrid gene of claim 1 which consists of the $F_{RSV}$-$HN_{PIV-3}$ hybrid gene.

12. The hybrid gene of claim 11 contained in plasmid pD2 RF-NH.

13. The process of claim 7 wherein said multimeric hybrid gene consists of the $F_{RSV}$-$HN_{PIV-3}$ hybrid gene.

14. The process of claim 13 wherein said multimeric hybrid gene is contained in an expression vector which is plasmid pD2 RF-HN.

15. A vector for antigen delivery containing the multimeric hybrid gene of claim 1.

16. The vector of claim 15 which is a viral vector.

17. The vector of claim 16 wherein said viral vector is selected from poxviral, adenoviral and retroviral viral vectors.

18. The vector of claim 15 which is a bacterial vector.

19. The vector of claim 18 wherein said bacterial vector is selected from salmonella and mycobacteria.

20. The vector of claim 15 wherein the gene consists of the $F_{RSV}$-$HN_{PIV-3}$ hybrid gene.

\* \* \* \* \*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1844 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AAGTCAATAC CAACAACTAT TAGCAGTCAT ACGTGCAAGA ACAAGAAAGA AGAGATTCAA      60

AAAGCTAAAT AAGAGAAATC AAAACAAAAG GTATAGAACA CCCGAACAAC AAAATCAAAA     120

CATCCAATCC ATTTTAAACA AAAATTCCAA AAGAGACCGG CAACACAACA AGCACCAAAC     180

ACAATGCCAA CTTTAATACT GCTAATTATT ACAACAATGA TTATGGCATC TTCCTGCCAA     240

ATAGATATCA CAAAACTACA GCATGTAGGT GTATTGGTCA ACAGTCCCAA AGGGATGAAG     300

ATATCACAAA ACTTCGAAAC AAGATATCTA ATTTTGAGCC TCATACCAAA AATAGAAGAC     360

TCTAACTCTT GTGGTGACCA ACAGATCAAA CAATACAAGA GGTTATTGGA TAGACTGATC     420

ATCCCTCTAT ATGATGGATT AAGATTACAG AAAGATGTGA TAGTAACCAA TCAAGAATCC     480

AATGAAAACA CTGATCCCAG AACAAGACGA TCCTTTGGAG GGGTAATTGG AACCATTGCT     540

CTGGGAGTAG CAACCTCAGC ACAAATTACA GCGGCAGTTG CTCTGGTTGA AGCCAAGCAG     600

GCAAAATCAG ACATCGAAAA ACTCAAAGAA GCAATCAGGG ACACAAACAA AGCAGTGCAG     660

TCAGTTCAGA GCTCTATAGG AAATTTAATA GTAGCAATTA AATCAGTCCA AGATTATGTC     720

AACAACGAAA TGGTGCCATC GATTGCTAGA CTAGGTTGTG AAGCAGCAGG ACTTCAATTA     780

GGAATTGCAT TAACACAGCA TTACTCAGAA TTAACAAACA TATTTGGTGA TAACATAGGA     840

TCGTTACAAG AAAAAGGAAT AAAATTACAA GGTATAGCAT CATTATACCG CACAAATATC     900

ACAGAAATAT TCAACACATC AACAGTTGAT AAATATGATA TCTATGATCT ATTATTTACA     960

GAATCAATAA AGGTGAGAGT TATAGATGTT GATTTGAATG ATTACTCAAT CACCCTCCAA    1020

GTCAGACTCC CTTTATTAAC TAGGCTGCTG AACACTCAGA TCTACAAAGT AGATTCCATA    1080
```

```
TCATATAATA TCCAAAACAG AGAATGGTAT ATCCCTCTTC CCAGCCATAT CATGACGAAA    1140

GGGGCATTTC TAGGTGGAGC AGATGTCAAG GAATGTATAG AAGCATTCAG CAGTTATATA    1200

TGCCCTTCTG ATCCAGGATT TGTACTAAAC CATGAAATGG AGAGCTGCTT ATCAGGAAAC    1260

ATATCCCAAT GTCCAAGAAC CACGGTCACA TCAGACATTG TTCCAAGATA TGCATTTGTC    1320

AATGGAGGAG TGGTTGCAAA CTGTATAACA ACCACCTGTA CATGCAACGG AATCGACAAT    1380

AGAATCAATC AACCACCTGA TCAAGGAGTA AAAATTATAA CACATAAAGA ATGTAATACA    1440

ATAGGTATCA ACGGAATGCT GTTCAATACA AATAAAGAAG GAACTCTTGC ATTCTACACA    1500

CCAAATGATA TAACACTAAA TAATTCTGTT GCACTTGATC CAATTGACAT ATCAATCGAG    1560

CTTAACAAAG CCAAATCAGA TCTAGAAGAA TCAAAAGAAT GGATAAGAAG GTCAAATCAA    1620

AAACTAGATT CTATTGGAAA CTGGCATCAA TCTAGCACTA CAATCATAAT TATTTTAATA    1680

ATGATCATTA TATTGTTTAT AATTAATGTA ACGATAATTA CAATTGCAAT TAAGTATTAC    1740

AGAATTCAAA AGAGAAATCG AGTGGATCAA AATGACAAGC CATATGTACT AACAAACAAA    1800

TGACATATCT ATAGATCATT AGATATTAAA ATTATAAAAA ACTT                      1844
```

(2) INFORMATION FOR SEQ ID NO:2:

(i) SEQUENCE CHARACTERISTICS:
    (A) LENGTH: 539 amino acids
    (B) TYPE: amino acid
    (C) STRANDEDNESS: single
    (D) TOPOLOGY: linear (ii) MOLECULE TYPE:

(xi) SEQUENCE DESCRIPTION: SEQ ID NO:2:

```
Met Pro Thr Leu Ile Leu Leu Ile Ile Thr Thr Met Ile Met Ala Ser
1               5                   10                  15

Ser Cys Gln Ile Asp Ile Thr Lys Leu Gln His Val Gly Val Leu Val
                20                  25                  30

Asn Ser Pro Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Thr Asn
                85                  90                  95

Gln Glu Ser Asn Glu Asn Thr Asp Pro Arg Thr Arg Arg Ser Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Lys Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Asn Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205
```

```
Glu Leu Thr Asn Ile Phe Gly Asp Asn Ile Gly Ser Leu Gln Glu Lys
    210                 215                 220
Gly Ile Lys Leu Gln Gly Ile Ala Ser Leu Tyr Arg Thr Asn Ile Thr
225                 230                 235                 240
Glu Ile Phe Thr Thr Ser Thr Val Asp Lys Tyr Asp Ile Tyr Asp Leu
                245                 250                 255
Leu Phe Thr Glu Ser Ile Lys Val Arg Val Ile Asp Val Asp Leu Asn
            260                 265                 270
Asp Tyr Ser Ile Thr Leu Gln Val Arg Leu Pro Leu Leu Thr Arg Leu
        275                 280                 285
Leu Asn Thr Gln Ile Tyr Lys Val Asp Ser Ile Ser Tyr Asn Ile Gln
    290                 295                 300
Asn Arg Glu Trp Tyr Ile Pro Leu Pro Ser His Ile Met Thr Lys Gly
305                 310                 315                 320
Ala Phe Leu Gly Gly Ala Asp Val Lys Glu Cys Ile Glu Ala Phe Ser
                325                 330                 335
Ser Tyr Ile Cys Pro Ser Asp Pro Gly Phe Val Leu Asn His Glu Met
            340                 345                 350
Glu Ser Cys Leu Ser Gly Asn Ile Ser Gln Cys Pro Arg Thr Thr Val
        355                 360                 365
Thr Ser Asp Ile Val Pro Arg Tyr Ala Phe Val Asn Gly Gly Val Val
    370                 375                 380
Ala Asn Cys Ile Thr Thr Thr Cys Thr Cys Asn Gly Ile Asp Asn Arg
385                 390                 395                 400
Ile Asn Gln Pro Pro Asp Gln Gly Val Lys Ile Ile Thr His Lys Glu
                405                 410                 415
Cys Asn Thr Ile Gly Ile Asn Gly Met Leu Phe Asn Thr Asn Lys Glu
            420                 425                 430
Gly Thr Leu Ala Phe Tyr Thr Pro Asn Asp Ile Thr Leu Asn Asn Ser
        435                 440                 445
Val Ala Leu Asp Pro Ile Asp Ile Ser Ile Glu Leu Asn Lys Ala Lys
    450                 455                 460
Ser Asp Leu Glu Glu Ser Lys Glu Trp Ile Arg Arg Ser Asn Gln Lys
465                 470                 475                 480
Leu Asp Ser Ile Gly Asn Trp His Gln Ser Ser Thr Thr Ile Ile Ile
                485                 490                 495
Ile Leu Ile Met Ile Ile Ile Leu Phe Ile Ile Asn Val Thr Ile Ile
            500                 505                 510
Thr Ile Ala Ile Lys Tyr Tyr Arg Ile Gln Lys Arg Asn Arg Val Asp
        515                 520                 525
Gln Asn Asp Lys Pro Tyr Val Leu Thr Asn Lys
    530                 535

(2) INFORMATION FOR SEQ ID NO:3:

(i) SEQUENCE CHARACTERISTICS:
        (A) LENGTH: 1833 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AGACAAATCC AAATTCGAGA TGGAATACTG GAAGCATACC AATCACGGAA AGGATGCTGG        60

CAATGAGCTG GAGACGTCCA TGGCTACTAA TGGCAACAAG CTCACCAATA AGATAACATA       120
```

-continued

```
TATATTATGG ACAATAATCC TGGTGTTATT ATCAATAGTC TTCATCATAG TGCTAATTAA        180

TTCCATCAAA AGTGAAAAGG CTCATGAATC ATTGCTGCAA GACATAAATA ATGAGTTTAT        240

GGAAATTACA GAAAAGATCC AAATGGCATC GGATAATACC AATGATCTAA TACAGTCAGG        300

AGTGAATACA AGGCTTCTTA CAATTCGAGG TCATGTCCAG AATTATATAC CAATATCACT        360

GACACAACAG ATGTCAGATC TTAGGAAATT CATTAGTGAA ATTACAATTA GAAATGATAA        420

TCAAGAAGTG CTGCCACAAA GAATAACACA TGATGTGGGT ATAAAACCTT TAAATCCAGA        480

TGATTTTTGG AGATGCACGT CTGGTCTTCC ATCTTTAATG AAAACTCCAA AAATAAGGTT        540

AATGCCAGGG CCGGGATTAT TAGCTATGCC AACGACTGTT GATGGCTGTA TCAGAACTCC        600

GTCCTTAGTT ATAAATGATC TGATTTATGC TTATACCTCA AATCTAATTA CTCGAGGTTG        660

TCAGGATATA GGAAAATCAT ATCAAGTCTT ACAGATAGGG ATAATAACTG TAAACTCAGA        720

CTTGGTACCT GACTTAAATC CCAGGATCTC TCATACTTTT AACATAAATG ACAATAGGAA        780

GTCATGTTCT CTAGCACTCC TAAATACAGA TGTATATCAA CTGTGTTCAA CTCCCAAAGT        840

TGATGAAAGA TCAGATTATG CATCATCAGG CATAGAAGAT ATTGTACTTG ATATTGTCAA        900

TTATGATGGC TCAATCTCAA CAACAAGATT TAAGAATAAT AACATAAGCT TGATCAACC        960

TTATGCTGCA CTATACCCAT CTGTTGGACC AGGGATATAC TACAAAGGCA AATAATATT       1020

TCTCGGGTAT GGAGGTCTTG AACATCCAAT AAATGAGAAT GTAATCTGCA ACACAACTGG       1080

GTGTCCCGGG AAAACACAGA GAGACTGCAA TCAGGCATCT CATAGTCCAT GGTTTTCAGA       1140

TAGGAGGATG GTCAACTCTA TCATTGTTGT TGACAAAGGC TTAAACTCAA TTCCAAAATT       1200

GAAGGTATGG ACGATATCTA TGAGACAGAA TTACTGGGGG TCAGAAGGAA GGTTACTTCT       1260

ACTAGGTAAC AAGATCTATA TATATACAAG ATCCACAAGT TGGCATAGCA AGTTACAATT       1320

AGGAATAATT GATATTACTG ATTACAGTGA TATAAGGATA AAATGGACAT GGCATAATGT       1380

GCTATCAAGA CCAGGAAACA ATGAATGTCC ATGGGGACAT TCATGTCCAG ATGGATGTAT       1440

AACAGGAGTA TATACTGATG CATATCCACT CAATCCCACA GGGAGCATTG TGTCATCTGT       1500

CATATTAGAT TCACAAAAAT CGAGAGTGAA CCCAGTCATA ACTTACTCAA CAGCAACCGA       1560

AAGAGTAAAC GAGCTGGCCA TCCGAAACAG AACACTCTCA GCTGGATATA CAACAACAAG       1620

CTGCATCACA CACTATAACA AAGGATATTG TTTTCATATA GTAGAAATAA ATCAGAAAAG       1680

CTTAAACACA CTTCAACCCA TGTTGTTCAA GACAGAGGTT CCAAAAAGCT GCAGTTAATC       1740

ATAATTAACC GCAATATGCA TTAACCTATC TATAATACAA GTATATGATA AGTAATCAGC       1800

AATCAGACAA TAGACAAAAG GGAAATATAA AAA                                    1833
```

(2) INFORMATION FOR SEQ ID NO:4:

(i) SEQUENCE CHARACTERISTICS:
  (A) LENGTH: 572 amino acids
  (B) TYPE: amino acid
  (C) STRANDEDNESS: single
  (D) TOPOLOGY: linear (ii) MOLECULE TYPE:

(xi) SEQUENCE DESCRIPTION: SEQ ID NO:4:

```
Met Glu Tyr Trp Lys His Thr Asn His Gly Lys Asp Ala Gly Asn Glu
 1               5                  10                  15

Leu Glu Thr Ser Met Ala Thr Asn Gly Asn Lys Leu Thr Asn Lys Ile
            20                  25                  30

Thr Tyr Ile Leu Trp Thr Ile Ile Leu Val Leu Leu Ser Ile Val Phe
```

```
                35                  40                  45
Ile Ile Val Leu Ile Asn Ser Ile Lys Ser Glu Lys Ala His Glu Ser
 50                  55                  60
Leu Leu Gln Asp Ile Asn Asn Glu Phe Met Glu Ile Thr Glu Lys Ile
 65                  70                  75                  80
Gln Met Ala Ser Asp Asn Thr Asn Asp Leu Ile Gln Ser Gly Val Asn
                 85                  90                  95
Thr Arg Leu Leu Thr Ile Gln Ser His Val Gln Asn Tyr Ile Pro Ile
                100                 105                 110
Ser Leu Thr Gln Gln Met Ser Asp Leu Arg Lys Phe Ile Ser Glu Ile
                115                 120                 125
Thr Ile Arg Asn Asp Asn Gln Glu Val Leu Pro Gln Arg Ile Thr His
                130                 135                 140
Asp Val Gly Ile Lys Pro Leu Asn Pro Asp Asp Phe Trp Arg Cys Thr
145                 150                 155                 160
Ser Gly Leu Pro Ser Leu Met Lys Thr Pro Lys Ile Arg Leu Met Pro
                165                 170                 175
Gly Pro Gly Leu Leu Ala Met Pro Thr Thr Val Asp Gly Cys Ile Arg
                180                 185                 190
Thr Pro Ser Leu Val Ile Asn Asp Leu Ile Tyr Ala Tyr Thr Ser Asn
                195                 200                 205
Leu Ile Thr Arg Gly Cys Gln Asp Ile Gly Lys Ser Tyr Gln Val Leu
                210                 215                 220
Gln Ile Gly Ile Ile Thr Val Asn Ser Asp Leu Val Pro Asp Leu Asn
225                 230                 235                 240
Pro Arg Ile Ser His Thr Phe Asn Ile Asn Asp Asn Arg Lys Ser Cys
                245                 250                 255
Ser Leu Ala Leu Leu Asn Thr Asp Val Tyr Gln Leu Cys Ser Thr Pro
                260                 265                 270
Lys Val Asp Glu Arg Ser Asp Tyr Ala Ser Ser Gly Ile Glu Asp Ile
                275                 280                 285
Val Leu Asp Ile Val Asn Tyr Asp Gly Ser Ile Ser Thr Thr Arg Phe
                290                 295                 300
Lys Asn Asn Asn Ile Ser Phe Asp Gln Pro Tyr Ala Ala Leu Tyr Pro
305                 310                 315                 320
Ser Val Gly Pro Gly Ile Tyr Tyr Lys Gly Lys Ile Ile Phe Leu Gly
                325                 330                 335
Tyr Gly Gly Leu Glu His Pro Ile Asn Glu Asn Val Ile Cys Asn Thr
                340                 345                 350
Thr Gly Cys Pro Gly Lys Thr Gln Arg Asp Cys Asn Gln Ala Ser His
                355                 360                 365
Ser Pro Trp Phe Ser Asp Arg Arg Met Val Asn Ser Ile Ile Val Val
370                 375                 380
Asp Lys Gly Leu Asn Ser Ile Pro Lys Leu Lys Val Trp Thr Ile Ser
385                 390                 395                 400
Met Arg Gln Asn Tyr Trp Gly Ser Glu Gly Arg Leu Leu Leu Leu Gly
                405                 410                 415
Asn Lys Ile Tyr Ile Tyr Thr Arg Ser Thr Ser Trp His Ser Lys Leu
                420                 425                 430
Gln Leu Gly Ile Ile Asp Ile Thr Asp Tyr Ser Asp Ile Arg Ile Lys
                435                 440                 445
Trp Thr Trp His Asn Val Leu Ser Arg Pro Gly Asn Asn Glu Cys Pro
450                 455                 460
```

```
Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Arg Asn Arg Thr Leu Ser Ala
        515                 520                 525

Gly Tyr Thr Thr Thr Ser Cys Ile Thr His Tyr Asn Lys Gly Tyr Cys
    530                 535                 540

Phe His Ile Val Glu Ile Asn Gln Lys Ser Leu Asn Thr Leu Gln Pro
545                 550                 555                 560

Met Leu Phe Lys Thr Glu Val Pro Lys Ser Cys Ser
                565                 570
```

(2) INFORMATION FOR SEQ ID NO:5:

(i) SEQUENCE CHARACTERISTICS:
        (A) LENGTH: 1886 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
ATGGAGTTGC CAATCCTCAA AGCAAATGCA ATTACCACAA TCCTCGCTGC AGTCACATTT    60

TGCTTTGCTT CTAGTCAAAA CATCACTGAA GAATTTTATC AATCAACATG CAGTGCAGTT   120

AGCAAAGGCT ATCTTAGTGC TCTAAGAACT GGTTGGTATA CTAGTGTTAT AACTATAGAA   180

TTAAGTAATA TCAAGGAAAA TAAGTGTAAT GGAACAGATG CTAAGGTAAA ATTGATGAAA   240

CAAGAATTAG ATAAATATAA AAATGCTGTA ACAGAATTGC AGTTGCTCAT GCAAAGCACA   300

CCAGCAGCAA ACAATCGAGC CAGAAGAGAA CTACCAAGGT TTATGAATTA TACACTCAAC   360

AATACCAAAA AAACCAATGT AACATTAAGC AAGAAAAGGA AAAGAAGATT TCTTGGTTTT   420

TTGTTAGGTG TTGGATCTGC AATCGCCAGT GGCATTGCTG TATCTAAGGT CCTGCACTTA   480

GAAGGAGAAG TGAACAAGAT CAAAAGTGCT CTACTATCCA CAAACAAGGC CGTAGTCAGC   540

TTATCAAATG GAGTTAGTGT CTTAACCAGC AAAGTGTTAG ACCTCAAAAA CTATATAGAT   600

AAACAATTGT TACCTATTGT GAATAAGCAA AGCTGCAGAA TATCAAATAT AGAAACTGTG   660

ATAGAGTTCC AACAAAAGAA CAACAGACTA CTAGAGATTA CCAGGGAATT TAGTGTTAAT   720

GCAGGTGTAA CTACACCTGT AAGCACTTAC ATGTTAACTA ATAGTGAATT ATTGTCATTA   780

ATCAATGATA TGCCTATAAC AAATGATCAG AAAAAGTTAA TGTCCAACAA TGTTCAAATA   840

GTTAGACAGC AAAGTTACTC TATCATGTCC ATAATAAAAG AGGAAGTCTT AGCATATGTA   900

GTACAATTAC CACTATATGG TGTGATAGAT ACACCTTGTT GGAAATTACA CACATCCCCT   960

CTATGTACAA CCAACACAAA AGAAGGGTCA AACATCTGTT TAACAAGAAC TGACAGAGGA  1020

TGGTACTGTG ACAATGCAGG ATCAGTATCT TTCTTCCCAC AAGCTGAAAC ATGTAAAGTT  1080

CAATCGAATC GAGTATTTTG TGACACAATG AACAGTTTAA CATTACCAAG TGAAGTAAAT  1140

CTCTGCAATG TTGACATATT CAATCCCAAA TATGATTGTA AAATTATGAC TTCAAAAACA  1200

GATGTAAGCA GCTCCGTTAT CACATCTCTA GGAGCCATTG TGTCATGCTA TGGCAAAACT  1260

AAATGTACAG CATCCAATAA AAATCGTGGA ATCATAAAGA CATTTTCTAA CGGGTGTGAT  1320
```

-continued

```
TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA ACTGAATAAA AATAGCACCT    1740

AATCATGTTC TTACAATGGT TTACTATCTG CTCATAGACA ACCCATCTAT CATTGGATTT    1800

TCTTAAAATC TGAACTTCAT CGAAACTCTT ATCTATAAAC CATCTCACTT ACACTATTTA    1860

AGTAGATTCC TAGTTTATAG TTATAT                                         1886
```

(2) INFORMATION FOR SEQ ID NO:6:

(i) SEQUENCE CHARACTERISTICS:
        (A) LENGTH: 594 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO:6:

```
Met Glu Leu Pro Ile Leu Lys Ala Asn Ala Ile Thr Thr Ile Leu Ala
1               5                  10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

```
                            245                     250                     255
Leu Leu Ser Leu Ile Asn Asp Met Pro Ile Thr Asn Asp Gln Lys Lys
                260                     265                     270

Leu Met Ser Asn Asn Val Gln Ile Val Arg Gln Ser Tyr Ser Ile
                275                     280                     285

Met Ser Ile Ile Lys Glu Glu Val Leu Ala Tyr Val Gln Leu Pro
    290                     295                     300

Leu Tyr Gly Val Ile Asp Thr Pro Cys Trp Lys Leu His Thr Ser Pro
305                     310                     315                     320

Leu Cys Thr Thr Asn Thr Lys Glu Gly Ser Asn Ile Cys Leu Thr Arg
                325                     330                     335

Thr Asp Arg Gly Trp Tyr Cys Asp Asn Ala Gly Ser Val Ser Phe Phe
                340                     345                     350

Pro Gln Ala Glu Thr Cys Lys Val Gln Ser Asn Arg Val Phe Cys Asp
                355                     360                     365

Thr Met Asn Ser Leu Thr Leu Pro Ser Glu Val Asn Leu Cys Asn Val
                370                     375                     380

Asp Ile Phe Asn Pro Lys Tyr Asp Cys Lys Ile Met Thr Ser Lys Thr
385                     390                     395                     400

Asp Val Ser Ser Ser Val Ile Thr Ser Leu Gly Ala Ile Val Ser Cys
                405                     410                     415

Tyr Gly Lys Thr Lys Cys Thr Ala Ser Asn Lys Asn Arg Gly Ile Ile
                420                     425                     430

Lys Thr Phe Ser Asn Gly Cys Asp Tyr Val Ser Asn Lys Gly Val Asp
                435                     440                     445

Thr Val Ser Val Gly Asn Thr Leu Tyr Tyr Val Asn Lys Gln Glu Gly
                450                     455                     460

Lys Ser Leu Tyr Val Lys Gly Glu Pro Ile Ile Asn Phe Tyr Asp Pro
465                     470                     475                     480

Leu Val Phe Pro Ser Asp Glu Phe Asp Ala Ser Ile Ser Gln Val Asn
                485                     490                     495

Glu Lys Ile Asn Leu Val Phe Pro Ser Asp Glu Phe Asp Ala Ser Ile
                500                     505                     510

Ser Gln Val Asn Glu Lys Ile Asn Gln Ser Leu Ala Phe Ile Arg Lys
                515                     520                     525

Ser Asp Glu Leu Leu His Asn Val Asn Ala Gly Lys Ser Thr Thr Asn
                530                     535                     540

Ile Met Ile Thr Thr Ile Ile Ile Glu Ile Ile Val Ile Leu Leu Ser
545                     550                     555                     560

Leu Ile Ala Val Gly Leu Leu Leu Tyr Cys Lys Ala Arg Ser Thr Pro
                565                     570                     575

Val Thr Leu Ser Lys Asp Gln Leu Ser Gly Ile Asn Asn Ile Ala Phe
                580                     585                     590

Ser Asn (2) INFORMATION FOR SEQ ID NO:7:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:
```

-continued

```
TGCAAACATG TCCAAAAACA AGGACCAACG CACCGCTAAG ACACTAGAAA AGACCTGGGA        60

CACTCTCAAT CATTTATTAT TCATATCATC GGGCTTATAT AAGTTAAATC TTAAATCTGT       120

AGCACAAATC ACATTATCCA TTCTGGCAAT GATAATCTCA ACTTCACTTA TAATTACAGC       180

CATCATATTC ATAGCCTCGG CAAACCACAA AGTCACACTA ACAACTGCAA TCATACAAGA       240

TGCAACAAGC CAGATCAAGA ACACAACCCC AACATACCTC ACTCAGGATC CTCAGCTTGG       300

AATCAGCTTC TCCAATCTGT CTGAAATTAC ATCACAAACC ACCACCATAC TAGCTTCAAC       360

AACACCAGGA GTCAAGTCAA ACCTGCAACC CACAACAGTC AAGACTAAAA ACACAACAAC       420

AACCCAAACA CAACCCAGCA AGCCCACTAC AAAACAACGC CAAAACAAAC CACCAAACAA       480

ACCCAATAAT GATTTTCACT TCGAAGTGTT TAACTTTGTA CCCTGCAGCA TATGCAGCAA       540

CAATCCAACC TGCTGGGCTA TCTGCAAAAG AATACCAAAC AAAAAACCAG GAAAGAAAAC       600

CACCACCAAG CCTACAAAAA AACCAACCTT CAAGACAACC AAAAAAGATC TCAAACCTCA       660

AACCACTAAA CCAAAGGAAG TACCCACCAC CAAGCCCACA GAAGAGCCAA CCATCAACAC       720

CACCAAAACA AACATCACAA CTACACTGCT CACCAACAAC ACCACAGGAA ATCCAAAACT       780

CACAAGTCAA ATGGAAACCT TCCACTCAAC CTCCTCCGAA GGCAATCTAA GCCCTTCTCA       840

AGTCTCCACA ACATCCGAGC ACCCATCACA ACCCTCATCT CCACCCAACA CAACACGCCA       900

GTAGTTATTA AAAAAAAAA                                                   920
```

(2) INFORMATION FOR SEQ ID NO:8:

(i) SEQUENCE CHARACTERISTICS:
    (A) LENGTH: 298 amino acids
    (B) TYPE: amino acid
    (C) STRANDEDNESS: single
    (D) TOPOLOGY: linear (ii) MOLECULE TYPE:

(xi) SEQUENCE DESCRIPTION: SEQ ID NO:8:

```
Met Ser Lys Asn Lys Asp Gln Arg Thr Ala Lys Thr Leu Glu Lys Thr
1               5                  10                  15

Trp Asp Thr Leu Asn His Leu Leu Phe Ile Ser Ser Gly Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Thr Ala Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Gln Thr Gln Pro Ser
    130                 135                 140

Lys Pro Thr Thr Lys Gln Arg Gln Asn Lys Pro Asn Lys Pro Asn
145                 150                 155                 160

Asn Asp Phe His Phe Glu Val Phe Asn Phe Val Pro Cys Ser Ile Cys
                165                 170                 175
```

```
Ser Asn Asn Pro Thr Cys Trp Ala Ile Cys Lys Arg Ile Pro Asn Lys
            180                 185                 190

Lys Pro Gly Lys Lys Thr Thr Lys Pro Thr Lys Lys Pro Thr Phe
            195                 200                 205

Lys Thr Thr Lys Lys Asp Leu Lys Pro Gln Thr Thr Lys Pro Lys Glu
210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
            275                 280                 285

Pro Ser Ser Pro Pro Asn Thr Thr Arg Gln
            290                 295
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCAATCAAA GGTCCTGTGA TAATAG                                        26

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CATGACTTGA TAATGAG                                                17

(2) INFORMATION FOR SEQ ID NO:11:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AATTCATGGA GTTGCTAATC CTCAAAGCAA ATGCAATTAC CACAATCCTC ACTGCAGTCA    60

CATTTTGTTT TGCTTCTGGT TCTAAG                                        86

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ACTGGCATCA ATCTAGCACT ACATGAG                                           27

(2) INFORMATION FOR SEQ ID NO:13:

(i) SEQUENCE CHARACTERISTICS:
            (A) LENGTH: 136 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

AATTCATGCC AACTTTAATA CTGCTAATTA TTACAACAAT GATTATGGCA TCTTCCTGCC        60

AAATAGATAT CACAAAACTA CAGCATGTAG GTGTATTGGT CAACAGTCCC AAAGGGATGA      120

AGATATCACA AAACTT                                                      136

(2) INFORMATION FOR SEQ ID NO:14:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

ATCATGGAGA TAATTAAAAT GATAACCATC TCGCAAATAA ATAAGTATTT TACTGTTTTC        60

GTAACAGTTT TGTAATAAAA AAACCTATAA ATAG                                   94

(2) INFORMATION FOR SEQ ID NO:15:

(i) SEQUENCE CHARACTERISTICS:
            (A) LENGTH: 141 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

ATCATGGAGA TAATTAAAAT GATAACCATC TCGCAAATAA ATAAGTATTT TACTGTTTTC        60

GTAACAGTTT TGTAATAAAA AAACCTATAA ATATTCCGGA ATTCAGATCT GCAGCGGCCG      120

CTCCATCTAG AAGGTACCCG G                                                141

(2) INFORMATION FOR SEQ ID NO:16:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

CATGACTAAT TCCATCAAAA GTGAAAAGGC T                                      31

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CAAGAAAAAG GAATAAAA                                                18

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ATTTCTGTGA TATTTGTGCG GTATAATGAT GCTATACCT                          39

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CAGGAGAAGG GTATCAAG                                                18

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AGGAGAAGGG TATCAAG                                                 17

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AGGACAAAAG                                                         10